United States Patent [19]

Noguchi et al.

[11] Patent Number: 5,233,191
[45] Date of Patent: Aug. 3, 1993

[54] METHOD AND APPARATUS OF INSPECTING FOREIGN MATTERS DURING MASS PRODUCTION START-UP AND MASS PRODUCTION LINE IN SEMICONDUCTOR PRODUCTION PROCESS

[75] Inventors: Minori Noguchi; Yukio Kembo; Hiroshi Morioka, all of Yokohama; Hiroshi Yamaguchi, Fujisawa; Makiko Kohno, Kawasaki; Yoshimasa Ohshima, Yokohama, all of Japan

[73] Assignee: Hitachi, Ltd., Tokyo, Japan

[21] Appl. No.: 679,317

[22] Filed: Apr. 2, 1991

[30] Foreign Application Priority Data

Apr. 2, 1990 [JP] Japan .................................. 2-084805
Jun. 26, 1990 [JP] Japan .................................. 2-165743

[51] Int. Cl.$^5$ ............................................. H01J 37/00
[52] U.S. Cl. .................................... 250/306; 250/307; 250/310; 437/7; 437/8
[58] Field of Search .................... 250/306, 310, 360.1, 250/358.1, 307; 437/7, 8, 939; 356/337, 338, 237

[56] References Cited

U.S. PATENT DOCUMENTS

| | | | |
|---|---|---|---|
| 3,771,880 | 11/1973 | Bennett | 356/446 |
| 3,930,155 | 12/1975 | Kanomata et al. | 250/309 |
| 4,332,833 | 6/1982 | Aspnes et al. | 427/8 |
| 4,441,248 | 4/1984 | Sherman et al. | 437/8 |
| 4,571,685 | 2/1986 | Kamoshida | 437/8 |
| 4,575,922 | 3/1986 | Nemiroff | 437/8 |
| 4,856,904 | 8/1989 | Akagawa | 356/400 |
| 4,939,363 | 7/1990 | Bando et al. | 250/306 |
| 4,963,500 | 10/1990 | Cogan et al. | 437/8 |
| 5,004,307 | 4/1991 | Kino et al. | 350/1.2 |
| 5,028,778 | 7/1991 | Ninomiya et al. | 250/305 |
| 5,055,679 | 10/1991 | Ninomiya et al. | 250/306 |

FOREIGN PATENT DOCUMENTS 1257725 9/1986 U.S.S.R. ............................. 250/306

OTHER PUBLICATIONS

"Simultaneous Observations of Partially Oxidized . . . " Komiya et al. J. Vac. Sci. Technol., vol. 12, No. 1, Jan./Feb. 1975.

Primary Examiner—Jack I. Berman
Assistant Examiner—Jim Beyer
Attorney, Agent, or Firm—Antonelli, Terry, Stout & Kraus

[57] ABSTRACT

Method and apparatus of detecting, analyzing and evaluating the content of foreign matters such as dusts and impurities contained in various materials, units, processes and environment standing for constituting components of a mass production line during mass production start-up and during mass production, in order to manage a semiconductor production process. A mass production off-line system including an apparatus for detecting, analyzing and evaluating the content of foreign matters during the mass production start-up is separated from the production line and installed independently thereof. Monitors for detection of foreign matters are provided at necessary locations in the production line and monitor data is evaluated through various units to manage the content of foreign matters in the production line, permitting efficient and economical mass production start-up and mass production. The kind of element of a foreign matter on sampling wafer detected in the mass production line is analyzed by means of STM/STS and the results are compared with a data base to effect identification. A foreign matter or a contaminant is detected by detecting a scatttered beam, of a light spot which scans the surface of a substrate. The detection of the scattered beam is carried out under the condition that Rayleigh scattering of the light spot on the light spot irradiation and reflection paths and Rayleigh scattering of the scattered beam on the scattered beam detection path are suppressed to a minimum. For the suppression of Rayleigh scattering, a low-pressure or low-temperature atmosphere may be used.

14 Claims, 18 Drawing Sheets

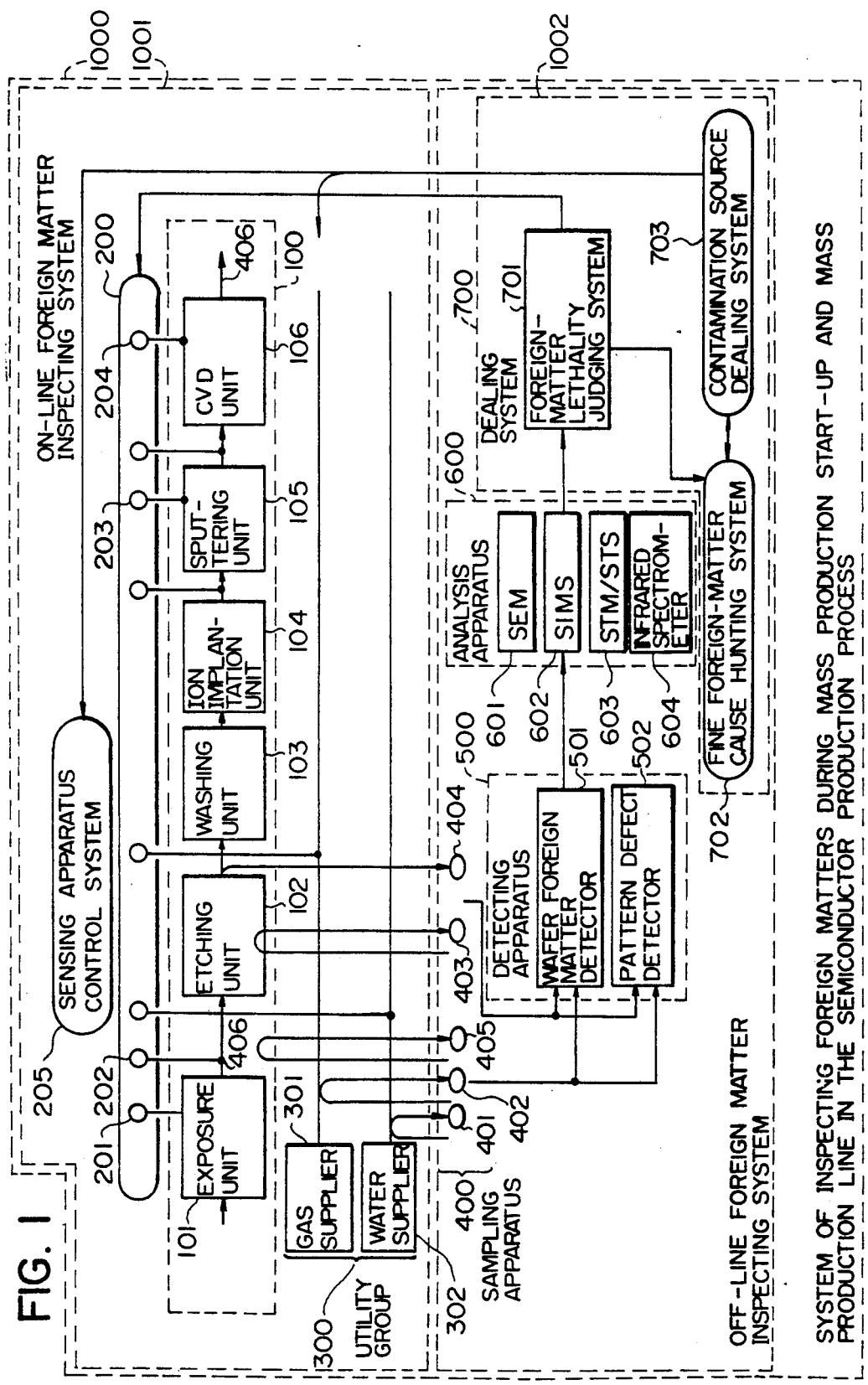

RAYLEIGH SCATTERING OF
AIR MOLECULES

FIG. 23

| | UNIT | USE MATERIAL | UNIT MATERIAL | SIZE OF FOREIGN MATTER | HYSTERESIS |
|---|---|---|---|---|---|
| | | . . | | | |
| 25 | ETCHING | CCl4 | SiO2 (Si,O) | φ10μm | |
| 26 | CVD | W | Fe, Ni | φ2μm | |
| 27 | OXIDATION | N2 | SiO2 (Si,O) | φ0.5μm | |
| 28 | RESIST COATER | RESIST (C,H,O) | Fe, Ni POLYETHYLENE | φ40μm | MUCH RESIST RESIDUAL |
| ⋮ | | . . | | | |
| 57 | | | | | |
| 8 | | | | | |
| ⋮ | | | | | |

METHOD AND APPARATUS OF INSPECTING FOREIGN MATTERS DURING MASS PRODUCTION START-UP AND MASS PRODUCTION LINE IN SEMICONDUCTOR PRODUCTION PROCESS

BACKGROUND OF THE INVENTION

The present invention relates to method and apparatus of inspecting foreign matters or substances during mass production start-up and mass production line in a semiconductor production process, which can detect and analyze foreign matters or substances (dusts, contaminative elements, impurities, and the like) generated during the mass production start-up and mass production line in the semiconductor production process and can undertake a countermeasure against the generation of foreign matters or substances.

In addition, the present invention also relates to contamination detecting method and apparatus for accurately detecting foreign matters and contaminants present on a substrate or contaminative elements present in a substrate as well as to a semiconductor production line in which the contamination detecting apparatus is installed at a predetermined layout in the line.

In the conventional semiconductor production process, a foreign matter present on a wafer is prone to be a cause of defects such as defective insulation and short-circuit of wiring and especially when fine foreign matters are present in fine structures of semiconductor devices formed on a wafer, these foreign matters are liable to break insulation films of capacitors and gate oxide films.

The foreign matters are introduced for various causes and in various conditions; for example, they are generated from movable parts of a transport unit, generated from human bodies, created from reaction of a process gas in a processing unit and contained as a mixture in chemicals or materials.

Under the circumstances, working for investigating a cause of generation of a foreign matter and undertaking a countermeasure therefor is involved as one of main workings during the start-up of mass production of LSI's and detection of the generated foreign matter and analysis of the kind of element provide a powerful means for hunting the cause of generation.

A technique for detecting and analyzing this kind of fine foreign matter present on a wafer has hitherto been developed, as disclosed in JP-A-63-135848. According to the technique, a laser beam is irradiated on a wafer and a scattered beam from a foreign matter deposited on the wafer is detected to determine the presence of the foreign matter. The thus determined foreign matter is analyzed using analysis technique such as laser photoluminescence or secondary X-ray spectroscopy (XMR).

Apart from the above literature, an article "TEM Observation of Defects Induced by Cu Contamination on Si(100) Surface", Japanese Journal of Applied Physics Vol. 27, No. 10, October, 1988, pp. L1819–L1821 introduces a phenomenon in which when a Si substrate is subjected to heat treatment, Cu in the Si substrate is diffused and precipitated.

Further, "Ohyoh Butsuri", Vol. 51, No. 11, 1982, pp. 1246–1254 discusses the relation between crystalline defect and precipitation of contaminants.

Incidentally, concomitant with advanced fine formation of LSI's, the presence of fine foreign matters raises at present practical problems in the semiconductor production. However, the techniques described in the aforementioned gazettes cannot afford to detect such fine foreign matters any more, especially, contamination due to heavy metal elements present in a wafer or on the surface of a wafer.

Accordingly, the advanced fine formation of semiconductor devices makes the aforementioned prior arts unsatisfactory to detect and analyze foreign matters generated during the start-up and line of mass production of fine-structure devices and to undertake a countermeasure therefor, and the advent of means for detecting and analyzing finer foreign matters is desired.

In addition, a detection/analysis equipment for practicing detection and analysis of the fine foreign matters is increased considerably in size and requires expense and space, hindering simplification of the mass production line. This is because in order to detect fine foreign matters, it is necessary to cause a beam to be scattered at a foreign matter more efficiently and focus a scattered beam and besides for the sake of analyzing finer foreign matters, expensive, large-scale apparatus such as Auger electron spectroscopy and secondary ion mass spectrometer (SIMS) are needed. Presumably, this tendency will be accelerated in future. Since the detection and analysis of the fine foreign matters is extremely time-consuming, the requisite apparatus must be used as efficiently as possible to reduce production cost. For simplification of the mass production line, a necessary and sufficient number of monitors must be installed at a necessary and sufficient number of locations.

Furthermore, in the prior art element analysis method particularly using an electron beam (for example, secondary X-ray spectroscopy), analysis is limited to foreign matters of about 0.5 μm because of the focusing efficiency of an electron beam. To cope with this problem, the focusing efficiency of the beam must be increased and to this end energy of the irradiation electron must be increased, raising a problem that the foreign matter to be analyzed is scattered. In a method using light such as infrared ray emission spectroscopy and fluorescence spectroscopy, the resolution smaller than a dimension d calculated from wavelength λ of light pursuant to the following equation is difficult to obtain:

where $\theta$ is a viewing angle of the detecting optics. Therefore, in the above foreign-matter analysis method, the spatial resolution must be increased.

SUMMARY OF THE INVENTION

An object of the invention is to provide method and apparatus of inspecting foreign matters during mass production start-up and mass production line in a semiconductor production line, which can clearly distinguish from each other the two states of the mass production start-up and the mass production in semiconductor production process to maximize the function of detecting, analyzing and evaluating foreign matters which is required during the mass production start-up and can simplify the production line during the mass production so as to reduce production cost.

Another object of the invention is to provide contamination detecting method and apparatus which can detect with high accuracies foreign matters of contaminants present on or in a substrate, especially, contamination due to heavy metal elements.

Still another object of the invention is to provide a semiconductor production line in which individual vacuum processing units for production of semiconductors, the degree of contamination of a substrate standing for an object to be processed and the presence or absence of foreign matters can be detected with ease.

According to one aspect of the invention, there are provided a method of detecting foreign matters during mass production start-up and mass production in a semiconductor production process as well as an apparatus therefor wherein when managing conditions for foreign matters in material, process, unit and environment are evaluated during the mass production start-up/mass production in the semiconductor production process, a system for detecting, analyzing and evaluating foreign matters during the mass production start-up/mass production is separated from the mass production line, and results obtained from the system are fed back to the mass production line to allow it to perform monitoring by using only a simple monitoring unit.

In the system for detecting, analyzing and evaluating foreign matters during the mass production start-up, a foreign matter on a sampling wafer is first detected and then the kind of element of the foreign matter is analyzed by means of a scanning tunneling microscope/-spectrometer (SIM/STS), and analysis data by the STM/STS is stored in advance as a data base which is compared with data of an analysis object to identify the kind of element of a foreign matter representative of the analysis object.

The method and apparatus of inspecting foreign matters during mass production start-up and mass production line in the semiconductor production process evaluate, during the mass production start-up, individual processes and equipments by means of an expensive, highperformance evaluating equipment in order to evaluate and debug the material, process, unit and design and during the mass production, simplify the equipments in the production line as possible, especially, reduce the number of items of inspection and evaluation so as to reduce the expense of the equipment and the time required for inspection and evaluation.

To this end, by using a foreign matter inspection/analysis system in which the sampling wafer is so contrived as to permit evaluation during the mass production start-up to proceed smoothly and rapidly, a cause of generation of a foreign matter is hunted to change the specification of inspection of delivered materials and undertake a countermeasure for a dust generation source in the equipment, the results are fed back to each of the material, process and unit to change the process specification liable to generate dusts to a process specification not liable to generate dusts, to prepare a design specification of a device immune to generated dusts and to prepare a specification according to which foreign matter (dust occurrence) monitors are installed as necessary at locations which are utilized for preparing specifications of inspection and evaluation of the mass production line and at which foreign matters tend to occur or only an increase or decrease in a specified foreign matter at a specified location is monitored. Namely, from the viewpoint of cost reduction, there are needs for limiting the number of foreign-matter monitors to a necessary minimum value. Then, by installing foreign-matter monitors in only units which are determined as problematic by the off-line inspecting system, the cost reduction can be accomplished. Specifically, it is conceivable to install monitors at the wafer outlet and inlet ports of the etching unit and CVD unit.

As described above, by separating the states of mass production start-up and mass production line from each other, the units for detecting, analyzing and evaluating foreign matters during the mass production start-up can be operated efficiently to effect the mass production start-up rapidly and at the same time, the equipments for inspection and evaluation of foreign matters (generated dusts) used during the mass production line can be constructed as necessarily simplified monitoring units to simplify the mass production line. Further, by designing a sampling wafer used during the mass production start-up such that the sampling interval can be decreased to reduce the sampling time, many pieces of highly-accurate foreign-matter occurrence data can be collected to expedite finding of troubled locations, thereby further decreasing the start-up period.

The technique of STM/STS used for analyzing the kind of elements of foreign matters during the mass production start-up has hitherto been available but it has been considered as being unable to identify the kind of element of a specimen and has not been used for production of LSI's. However, the present inventors notice that when considering the fact that the kinds of foreign matters generated in production of LSI's are limited, even the conventional technique of STM/STS can be applicable.

Thus, the system is so designed that STM/STS spectra of elements having a possibility of being generated as dusts in the production line are stored as a data base and the data base is compared with data of an object to be inspected to permit analysis of dusts, thereby ensuring that the kind of element of a foreign matter can be identified to evaluate a generation source and undertake a countermeasure.

According to another aspect of the invention, a contamination detecting apparatus of detecting a foreign matter or a contaminant present on a substrate by detecting a scattered beam from the foreign matter or contaminant is attached with an atmosphere setting-/maintaining system for causing a scattered beam detection system to detect the scattered beam from the foreign matter or contaminant in a specified atmosphere by suppressing unwanted Rayleigh scattering, and is further attached with a substrate heating system for preheating the substrate to cause contaminative elements to be diffused and precipitated prior to contamination detection.

The second object of the invention can be accomplished by installing the contamination detecting apparatus constructed as above at the substrate outlet/ inlet ports of each vacuum processing unit for semiconductor production.

Generally, when a foreign matter of a contaminant is present on the surface of a substrate whose whole surface is scanned with a light spot, a scattered beam is generated at a position where the foreign matter or contaminant exists and the foreign matter or contaminant can be detected by detecting the scattered beam. However, if in ordinary atmosphere of air a light spot is irradiated on the substrate surface and reflected therefrom or a scattered beam from a foreign matter or a contaminant is detected, the light spot interacts with air molecules on the irradiation and reflection paths to undergo unwanted Rayleigh scattering and the scattered beam interacts with air molecules midway the path to the scattered beam detection system to undergo unwanted Rayleigh scattering, with the result that the scattered beam cannot be detected at a high S/N ratio.

Accordingly, by detecting the scattered beam under a specified atmosphere condition capable of suppressing the unwanted Rayleigh scattering to a minimum (specifically, low pressure or low temperature atmosphere condition or atmosphere condition of a specified gas having less Rayleigh scattering effect than air), the foreign matter or contaminant can be detected with high accuracies.

When a substrate is heated prior to detection of foreign matters or contaminants by scanning the substrate with a laser beam, contaminative elements such as heavy metals present in the substrate are diffused to be precipitated collectively on the substrate surface, making it possible to detect the contaminative elements present in the substrate. In this case, by etching the substrate with a process gas after completion of heating or by heating a substrate formed in its surface with a low potential portion or a small flaw, contamination can be emphasized considerably and can therefore be detected with higher accuracies.

Generally, the contamination detecting apparatus is so constructed as to detect a scattered beam from a foreign matter or a contaminant present on a substrate. Especially when the contamination detecting apparatus for detecting a foreign matter or a contaminant present on a substrate by detecting a scattered beam from the foreign matter or contaminant is attached with an atmosphere setting/maintaining system for causing a scattered beam detection system to detect the scattered beam from the foreign matter or contaminant in a specified atmosphere by suppressing unwanted Rayleign scattering, not only the generation of unwanted Rayleign scattering on the light spot irradiation path and reflection path can be suppressed but also Rayleigh scattering on the scattered beam detection path for the scattered beam necessary for detecting of the foreign matter or contaminant can be suppressed, with the result that the foreign matter or contaminant can be detected with high accuracies. In addition, when the contamination detecting apparatus provided with the atmosphere setting/maintaining system is attached with a substrate heating system for pre-heating the substrate prior to contamination detection, contaminative elements present in the substrate can be detected easily for the reasons described previously.

Furthermore, when the contamination detecting apparatus constructed as above are installed at the substrate outlet/inlet ports of individual vacuum processing units acting as constituting components in the semiconductor production line, contamination can be managed before and after treatment at each vacuum processing unit

BRIEF DESCRIPTION OF THE DRAWINGS

FIG. 1 is a schematic block diagram showing an embodiment of method and apparatus of inspecting foreign matters during mass production start-up and mass production line in the semiconductor production process, accoridng to the invention;

FIG. 23 is a table indicating the relation among various factors used to reduce a foreign matter generation source.

DESCRIPTION OF THE PREFERRED EMBODIMENTS

Figure 2A:
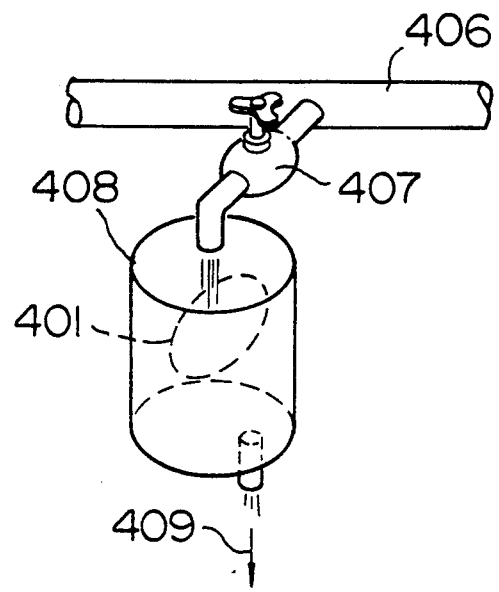
FIGS. 2A to 2D are perspective views showing an embodiment of a sampling apparatus in FIG. 1.

FIG. 1 is a schematic block diagram showing an embodiment of a method of inspecting foreign matters or substances during mass production start-up and mass production line in the semiconductor production process as well as an arrangement therefor. Referring to FIG. 1, an arrangement of inspecting foreign matters during mass production start-up and mass production line in the semiconductor production process comprises: a semiconductor production apparatus group 100 including an exposure unit 101, an etching unit 102, a washing unit 103, an ion implantation unit 104, a sputtering unit 105, and a CVD unit 106; a sensing apparatus 200 including a temperature sensor 201, a dust occurrence monitor 202, a pressure sensor 203 and an in-vacuum dust occurrence monitor 204; a sensing apparatus control system 205; a utility group 300 including a gas supplier 301 and a water supplier 302; a sampling apparatus 400 including a water quality sampling wafer 401, a gas sampling wafer 402, an in-unit sampling wafer 403, a device wafer 404 and an atmosphere sampling wafer 405; a detecting apparatus 500 including a wafer foreign matter detector 501 and a pattern defect detector 502; an analysis apparatus 600 including a scanning electron microscope (SEM) 601, a secondary ion mass spectrometer (SIMS) 602, a scanning tunneling microscope/spectrometer (STM/STS) 603, and an infrared spectrometer 604; and a dealing system 700 including a foreign-matter lethality judging system 701, a fine foreign-matter cause hunting system 702 and a contamination source dealing system 703. The above constituting components may be sorted into an on-line foreign matter inspecting system 1001 corresponding to mass production line and an off-line foreign matter inspecting system 1002 corresponding to mass production start-up line, these systems being combined together to establish a system 1000 of inspecting foreign matters during mass production start-up and mass production line in the semiconductor production process.

Figure 2B:
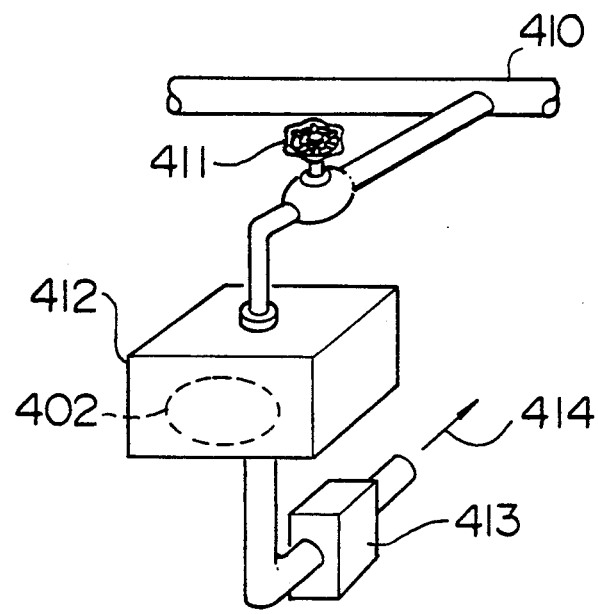
Figure 2C:
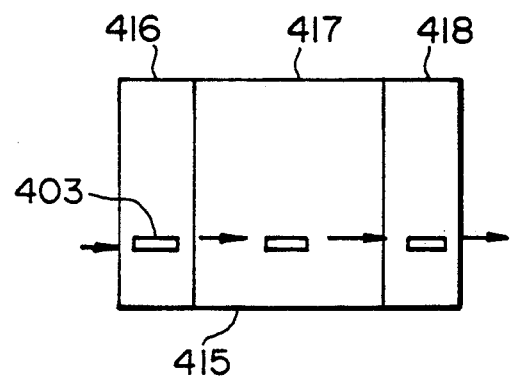
Figure 2D:
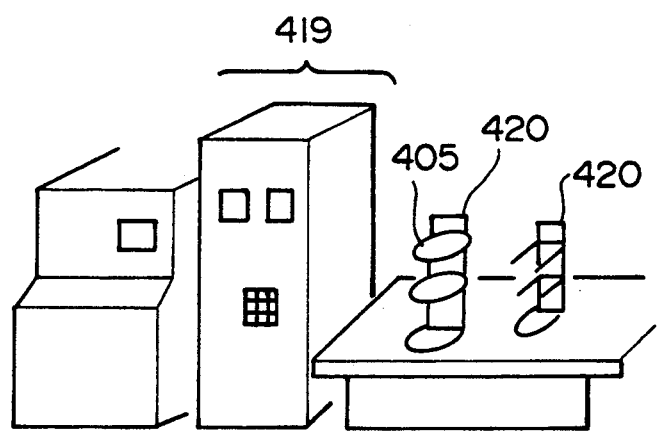

FIGS. 2A to 2D are perspective views showing the construction of an embodiment of the sampling apparatus shown in FIG. 1. Referring to FIGS. 2A to 2D, the water quality sampling wafer 401 shown in FIG. 2A is placed in a buffer chamber 408 of a unit comprised of a pure water piping 406, a faucet 407 for sampling, the buffer chamber 408 and a drainage means 409, in order to sample foreign matters in pure water supplied from the water supplier 302 shown in FIG. 1. The gas sampling wafer 402 shown in FIG. 2B is likewise placed in a buffer chamber 412 of a unit comprised of a gas piping 410, a valve 411 for sampling. The buffer chamber 412, a rotary pump 413 and an evacuation means 414, in order to sample foreign matters in a gas supplied from the gas supplier 301 shown in FIG. 1. The sampling wafer 403 in a process unit 415 (such as etching unit 102 of FIG. 1) shown, in sectional form, in FIG. 2C passes through a loader chamber 416, a process chamber 417 and an unloader chamber 418 of the process unit 415 to sample foreign matters generated therein. Practically, the sampling operation may conceivably be either effected or not effected in the process chamber 417. The device wafer 404 is a wafer which is actually processed in the process unit 415 (such as etching unit 102). The atmosphere sampling wafer 405 shown in FIG. 2D is carried on a sampling stand 420 in process atmosphere 419 to sample foreign matters in the process atmosphere 419.

Figure 3:
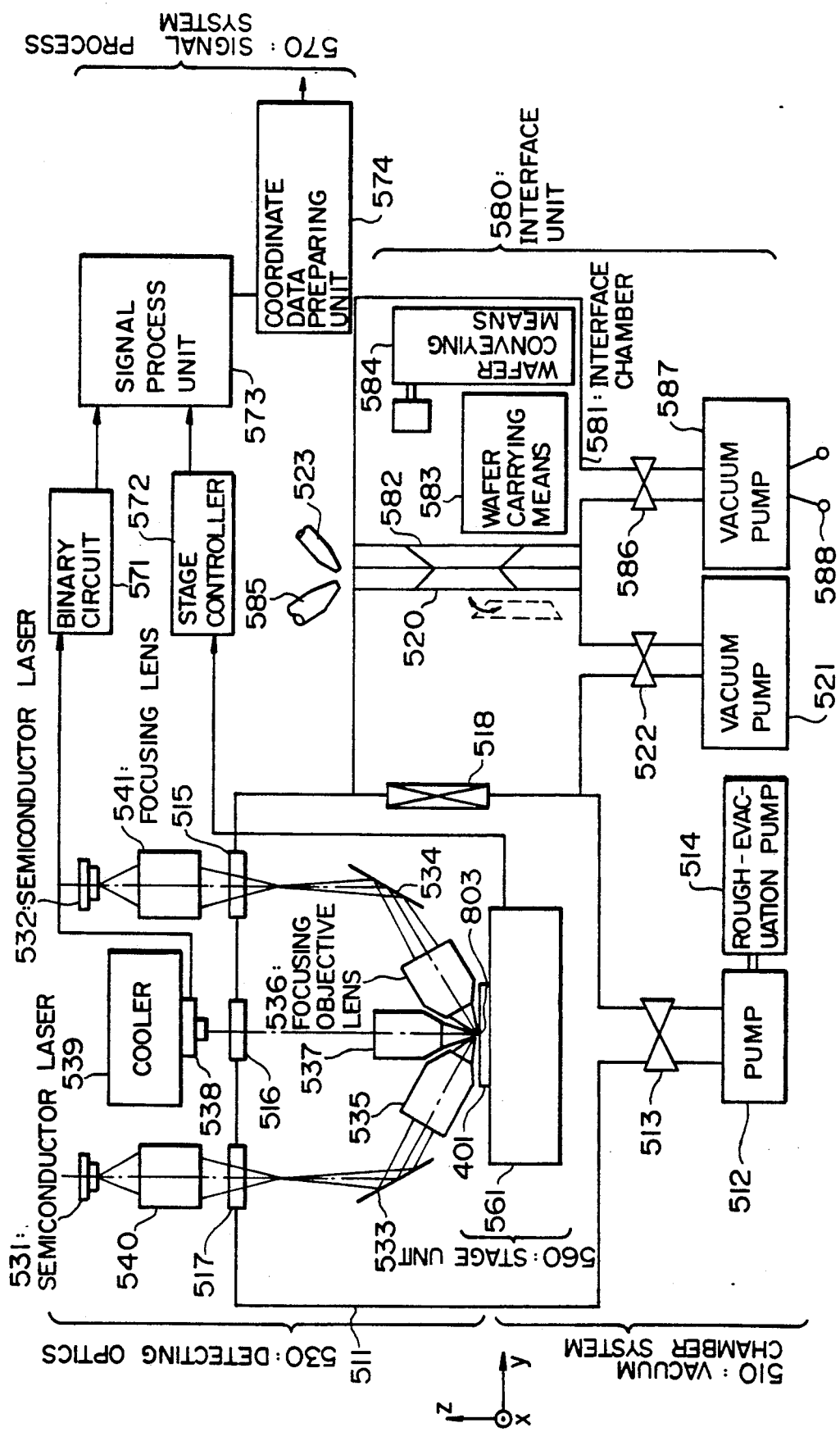
FIG. 3 is a schematic block diagram showing an embodiment of a detecting apparatus in FIG. 1.

FIG. 3 is a schematic block diagram illustrating an embodiment of the detecting apparatus 500 shown in FIG. 1. Referring to FIG. 3, the detecting apparatus 500 comprises: a vacuum chamber system 510 including a vacuum chamber 511, a high vacuum pump 512 such as an ion pump or a turbo molecular pump, a valve 513, a roughevacuation pump 514 such as a rotary pump, windows 515, 516 and 517, gate valves 518 and 520, a vacuum pump 521, a valve 522 and a gas blasting nozzle 523; a detecting optics 530 including semiconductor lasers 531 and 532, focusing lenses 540 and 541, mirrors 533 and 534, focusing objective lenses 535 and 536, a detecting objective lens 537, a detector 538 and a cooler 539; a stage unit 560 having an XYZ stage 561; a signal process system 570 including a binary circuit 571, a stage controller 572, a signal process unit 573 and a coordinate data preparing unit 574; and an interface unit 580 including an interface chamber 581, a load lock 582, wafer carrying means 583, wafer converying means 584, a gas blasting nozzle 585, a valve 586, a vacuum pump 587 and a truck 588.

Figure 4:
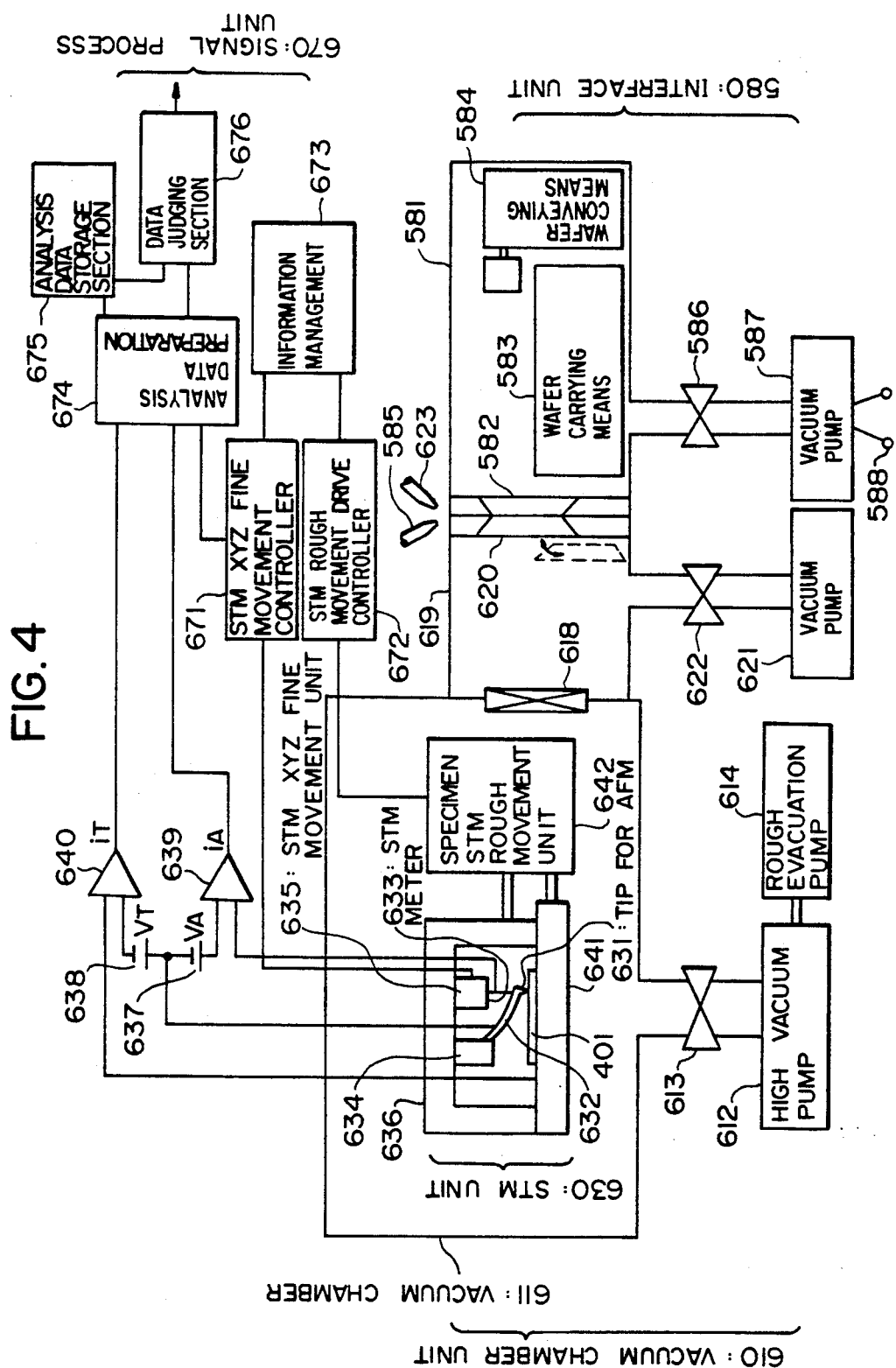
FIG. 4 is a schematic block diagram showing an embodiment of an analysis apparatus in FIG. 1.

FIG. 4 is a schematic block diagram illustrating an embodiment of the analysis apparatus 600. Referring to FIG. 4, the analysis apparatus comprises: a vacuum chamber unit 610 including a vacuum chamber 611, a high vacuum pump 612 such as an ion pump or a turbo molecular pump, a rough-evacuation pump 614 such as a rotary pump, a gate valve 613, a preliminary vacuum chamber 619, a gate valve 620, a vacuum pump 621, a valve 622 and a gas blasting nozzle 623; an STM unit 630 including a tip 631 for an atomic force microscope (AFM), a weak force reactive lever 632, a lever fixture 634, an STM meter 633, an STM XYZ fine movement unit 635, an AFM bias power supply 638, an STM bias power supply 637, current measuring means 639 and 640, a specimen pedestal 641, an STM unit arm 636, and a specimen STM rough drive unit 642; a signal process unit 670 including an STM XYZ fine movement unit controller 671, a specimen STM rough drive unit controller 672, an analysis data preparing unit 674, an analysis data storing unit 675, an analysis data judging unit 676 and an information managing unit 673; and an interface unit 580 which is identical to the detecting apparatus 500 of FIG. 3.

The function and operation of the sampling apparatus 400 shown in FIGS. 2A to 2D, detecting apparatus 500 of FIG. 3 and analysis apparatus 600 of FIG. 4, which form the kernel of the off-line foreign matter inspecting system 1002, will now be described.

In the sampling apparatus 400 shown in FIGS. 2A to 2D, the unit of FIG. 2A, for example, evaluates pure water which is supplied from the water supplier 302 of FIG. 1 and which is used for various production processes by pouring the pure water to be used onto the sampling wafer 401 to deposit foreign matters in the pure water on the sampling wafer 401. Otherwise, the sampling wafer 403 is passed through the process unit 415 (for example, etching unit 102) of FIG. 2 having a vacuum process chamber so that foreign matters generated in the process unit 415 may be deposited on the sampling wafer 403; or the sampling wafer 405 is placed at a desired position in the clean room of the process atmosphere 419 so that foreign matters in the atmosphere may be deposited on the wafer 405. Details of the sampling wafers 401 to 405 used herein will now be described with reference to FIGS. 5, 6A to 6C, 7A to 7D and 8A to 8D.

Figure 5:
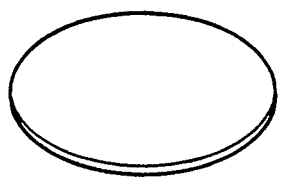
FIG. 5 is a perspective view showing a mirror surface wafer standing for a sampling wafer in FIG. 1.

FIG. 5 is perspective view showing a mirror surface wafer of the sampling wafers 401 to 405 in FIG. 1 and FIGS. 2A to 2D. The mirror surface wafer is obtained by polishing the wafer surface to a mirror surface and it has an advantrge that the detection and analysis of foreign matters is the most immune from the influence of the wafer surface.

Figure 6A:
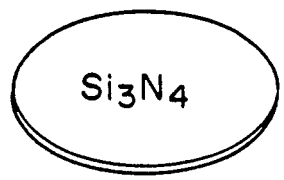
FIGS. 6A to 6C are perspective views respectively showing a wafer formed with $Si_3N_4$ film, a wafer formed with poly-Si film and a wafer formed with Al film which stand for the sampling wafer in FIG. 1.
Figure 6B:
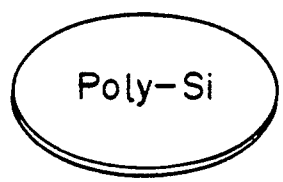
Figure 6C:
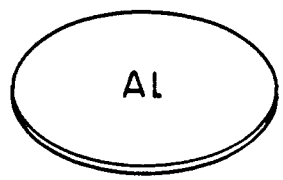

FIGS. 6A, 6B and 6C are perspective views respectively illustrating sampling wafers as shown in FIG. 1 and FIGS. 2A to 2D which are formed with $Si_3N_4$, poly-Si and Al films, respectively. Each of the sampling wafers shown in FIGS. 6A to 6C is made of the same material as that of a wafer for an object to be evaluated. Therefore when evaluating, for example, a washing tank (such as washing unit 103) with a sampling wafer, the deposition state of foreign matters on the sampling wafer during washing coincides with the state of foreign matters deposited on a wafer to be washed of the same material to permit highly accurate evaluation of the washing tank. The sampling wafer may also be passed through a film forming unit in the succeeding film forming process to evaluate a condition of occurrence of foreign matters in the film forming unit.

Figure 7A:
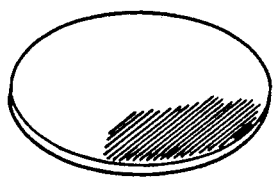
FIGS. 7A to 7D are perspective views showing wafers formed with patterns standing for the sampling wafer in FIG. 1.
Figure 7C:
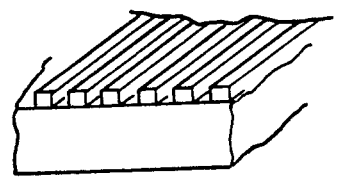
Figure 7B:
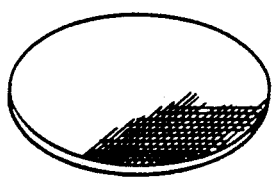
Figure 7D:
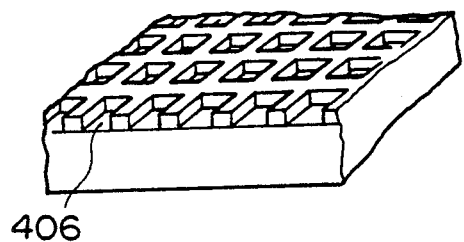
Figure 8A:
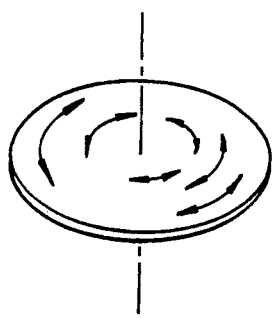
FIGS. 8A to 8D are perspective views showing lapping and scanning directions on the sampling wafer in FIG. 1.
Figure 8C:
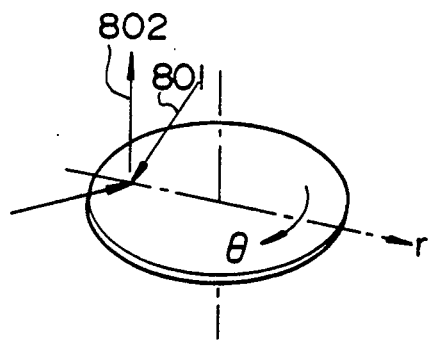
Figure 8B:
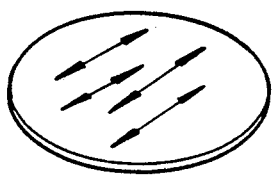
Figure 8D:
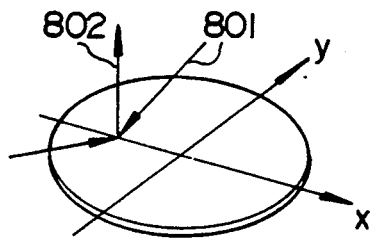

The sampling wafers 401 to 405 shown in FIG. 1 and FIGS. 2A to 2D may be formed with patterns as shown in perspective form in FIGS. 7A to 7D. Pattern configurations on these wafers model patterns of actual devices and wafers of FIGS. 7A and 7B are respectively formed with patterns which are illustrated in partial enlarged form in FIGS. 7C and 7D. The sampling wafers of FIGS. 7A to 7D take into account the dependency of foreign-matter deposition upon the pattern configuration and are effective to accurately reproduce a condition of deposition of foreign matters on an actual device. In addition, when the wafer formed with the regular pattern configuration as described above is used for foreign matter detection, diffracted beams from the pattern can be shielded with high accuracy by using, for example, a space filter, thereby ensuring highly accurate detection of foreign matters. More specifically, with the FIG. 7A wafer having the FIG. 7C pattern, diffracted beams from the pattern can be prevented from impinging on the detecting objective lens 537 of the detecting optics by placing the wafer 401 such that the longitudinal direction of the pattern coincides with illustrated y direction of the XYZ stage 561 of the detecting apparatus 500 shown in FIG. 3. With the FIG. 7B wafer having the FIG. 7D pattern, the wafer is placed such that the direction of the pattern coincides with a direction which is rotated by 45 degrees from the illustrated y direction of the XYZ stage 561 of the detecting apparatus 500 shown in FIG. 3. In this case, the presence of scattered beams from crossings 406 of the FIG. 7D pattern makes the detection of foreign matters with the FIG. 7D pattern less accurate than with the FIG. 7C pattern but from the stand point of modeling actual devices, the FIG. 7D pattern reflects actual devices more accurately than the FIG. 7C pattern, making it possible to achieve higher sampling accuracy, in evaluating the washing tank or the like.

FIGS. 8A, 8B, 8C and 8D are perspective views showing the lapping direction during production and the scanning direction during inspection of the sampling wafers 401 to 405 shown in FIG. 1 and FIGS. 2A to 2D. Typically, during the final finishing of production of wafers, the wafer surface is polished to mirror surface and conceivably, the polishing direction is oriented to the rotation direction about the central axis of wafer as shown at arrow in FIG. 8A, to the y direction of wafer as shown at arrow in FIG. 8B or to the resultant direction of the directions shown in FIGS. 8A and 8B. Accordingly, many fine flaws are formed in the wafer surface in a direction parallel to the wafer polishing direction shown in FIG. 8A or 8B; or with the wafer polished in the resultant direction of the polishing directions shown in FIGS. 8A and 8B, there are flaws formed mainly in the resultant direction. These flaws hinder fine particles of foreign matters on the wafer surface from being detected. Accordingly, when inspection of foreign matters on the wafer surface is carried out by scanning the beam in r or θ direction or x or y direction, the flaw direction can be kept to be constant with respect to irradiation direction 801 and detection direction 802 of the light beam during inspection, with the result that beams diffracted mainly in the flaw direction can be cut.

The sampling wafers 401 to 405 deposited with foreign matters in the sampling apparatus 400 shown in FIG. 1 and FIGS. 2A to 2D are sent to the detecting apparatus 500. If the wafer is scheduled to be subjected to vacuum treatment and its exposure to atmosphere is not desired, the sampling wafers 401 to 405 can be conveyed into the vacuum chamber 511 by using the interface unit 580 of FIG. 3. Each of the sampling wafers 401 to 405 is required to be applied with alignment marks serving as coordinate criteria for coupling to be effected subsequently between the detecting apparatus 500 and the analysis apparatus 600. Such alignment marks may be of any type and these marks have to be applied at least two locations to meet coordinates x, y and θ needed for coordinate alignment.

In the detecting apparatus 500 of FIG. 3, a sampling wafer 401 brought into the wafer foreign matter detector 501 is carried on the XYZ stage 561 and irradiated at its measuring point 803 with beams from the semiconductor lasers 531 and 532 by means of the focusing objective lenses 535 and 536 of the irradiating or illumination optics. A scattered beam from a foreign matter at the measuring point 803 is focused on the detector 538 by means of the detecting objective lens 537. A formed image undergoes photoelectric conversion at the detector 538 so as to be converted into an electrical signal which is converted by the binary circuit 571 into a binary signal sent to the signal process unit 573. During inspection, the XYZ stage 561 is controlled by driving a Z stage such that the focal point of the detecting objective lens 537 of the detecting optics coincides with the measuring point 803 and at the same time the stage 561 is scanned in the XY directions by means of XY stages. As a result, the entire surface of the wafer 401 can be inspected. In the presence of a foreign matter, the signal process unit 573 fetches coordinates of the XY stages from the stage controller 572 and the coordinate data preparing unit 574 prepares coordinate data which in turn is sent to the analysis apparatus 600.

In the detecting apparatus 600 of FIG. 4, analysis using the STM/STS 603 is carried out as will be described below. The analysis using the STM, that is, STS (Scanning Tunneling Spectroscopy) is discussed in detail in, for example, "Application of Scanning Tunneling Microscope/Spectroscopy (STM/STS) to Study on Catalyzer Surface", "Surface", Vol. 26, No. 6 (1988), pp. 384–391. This literature describes that the STM/STS assures measurement with high spatial resolution but disadvantageously it cannot identify the kind of element. According to this literature, information which can be collected by the STM includes only bias voltage V, tunnel current i and a change $\Delta Z$ in the distance between probe tip and specimen and by calculating $d\theta/dz$ from the information, work function $\phi$ in the specimen surface can be calculated. The above literature does not clarify the reason of failure to identify the kind of element but conceivably, the identification of the kind of element cannot be accomplished for the following reason. Namely, the work function $\phi$ is a function of the kind of element and the state of binding of element and hence many kinds of elements and many binding states of element can be thought of for one work function $\phi$. Therefore even when the work function $\phi$ can be determined, the kind of element and the state of binding of element cannot be determined. However, the present inventors notice the fact that the kinds of elements which are possibly introduced into the production line of semiconductors are limited, to conclude that an object to be measured can be identified as an element which is selected from a limited number of elements, on the basis of the work function $\phi$ obtained by the STM/STS in the followng manner.

According to, for example, "Scanning Tunneling Microscope", "Ohyoh Butsuri", Vol. 56, No. 9, pp. 1126–1137, tunnel current $i_T$ detectable by the ammeter 640 of the analysis apparatus 600 can be calculated pursuant to the following equation:

$$i_T \propto J_T = \frac{e^2}{h} \cdot V_T \cdot \frac{1}{2\pi} \cdot \frac{2\pi \sqrt{2m\phi}}{h} \times \frac{1}{Z} \cdot \exp\left(-2Z \frac{2\pi \sqrt{2m\phi}}{h}\right) \quad (2)$$

where $J_T$ is tunnel current density, e is electric charge of electron, h is Planck's constant, m is mass of electron and $\phi$ is work function. Since, in equation (2), $V_T$ is bias voltage of the bias power supply 638, the tunnel current $i_T$ is measurable and only Z and $\phi$ are unknown quantities, the work function $\phi$ can be calculated when the distance between probe tip and specimen as represented by Z and Z+$\Delta$Z and the tunnel current $i_T$ are measured.

Figure 9:
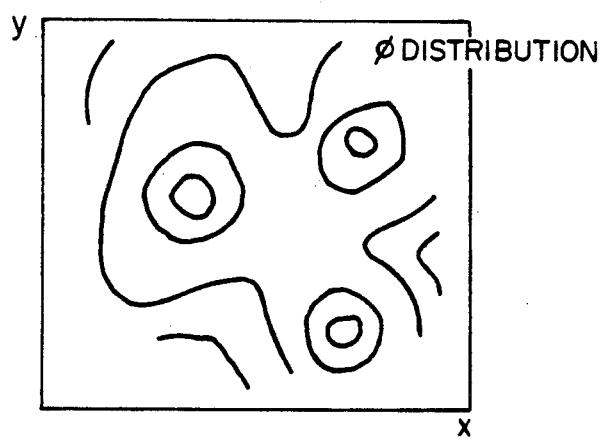
FIG. 9 is a graph showing an x-y distribution of work function in a specimen.

FIG. 9 shows an xy distribution of work function in the specimen 401 in the analysis apparatus 600 of FIG. 4. With the analysis apparatus 600 of FIG. 4, tunnel current $i_T$ in the specimen 401 is measured and work function $\phi$ is calculated pursuant to equation (2) to obtain a distribution of work function $\phi$ on xy plane as shown in FIG. 9, the distribution indicating in the atomic order a distribution of materials in the specimen 401.

Figure 10:
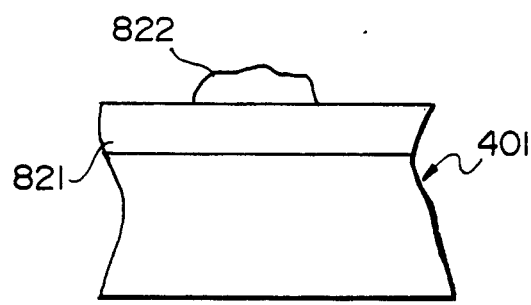
FIG. 10 is a sectional view of the FIG. 4 specimen.

FIG. 10 shows in sectional form the specimen 401 in the analysis apparatus 600 of FIG. 4. When the specimen 401 has a thin film 821 on which a foreign matter 822 is deposited to form a structure as shown in FIG. 10, the value of the work function $\phi$ in the specimen 401 of the FIG. 4 analysis apparatus 600 is that of a work function in the whole system inclusive of the thin film 821 and foreign matter 822. Therefore, the data base for the xy distribution of work function $\phi$ in speciment 401 shown in FIG. 9 is different for materials of the foundation and hence the work function has to be measured in advance for various kinds of materials of the foundation. Conversely, the material of the specimen 401 can be deduced from the data prepared in advance for various foundations.

Figure 11:
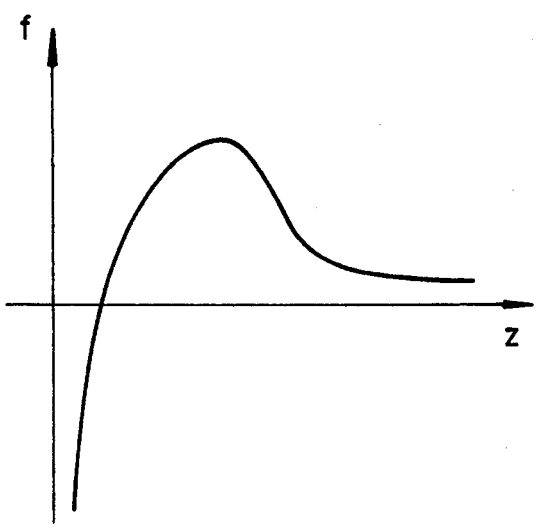
FIG. 11 is a graph showing the relation between the distance of the AFM tip from the specimen and interatomic force in the FIG. 4 apparatus.

FIG. 11 graphically shows a function between interatomic force f and distance Z of the AFM tip 631 from the specimen 401 in the analysis apparatus of FIG. 4. With the FIG. 4 analysis apparatus 600, by controlling the Z direction of the STM tip 633 while keeping current $i_A$ constant, a distribution of force f interacting between the specimen 401 and the AFM tip 631 can be measured by means of the AFM tip 631 and the relation as shown in FIG. 11 can be obtained between the interatomic force f interacting between specimen 401 and AFM tip 631 and the distance Z between specimen 401 and AFM tip 631. According to, for example, "Introduction to Solid State Physics, 4-th Edition, Vol. 1" by Kittel, published by Maruzen Kabushiki-Kaisha, pp. 114–122, the f-z waveform is representative of the sum of coulomb force and repulsive force energy, thus having two parameters, and the two parameters determine the f-z waveform of FIG. 11. Given that the two parameters are $\alpha$ and $\beta$, the relation indicated by the following equation stands between the force f interacting between specimen 401 and AFM tip 631 and the distance Z between specimen 401 and AFM tip 631:

$$f \propto \exp\left(-\frac{Z}{\alpha}\right) - \frac{\beta}{Z}. \quad (3)$$

By measuring the force f for two distances Z, that is, at two coordinates Z of the AFM tip drive unit 635, values of the parameters $\alpha$ and $\beta$ can be calculated pursuant to equation (3).

Figure 12:
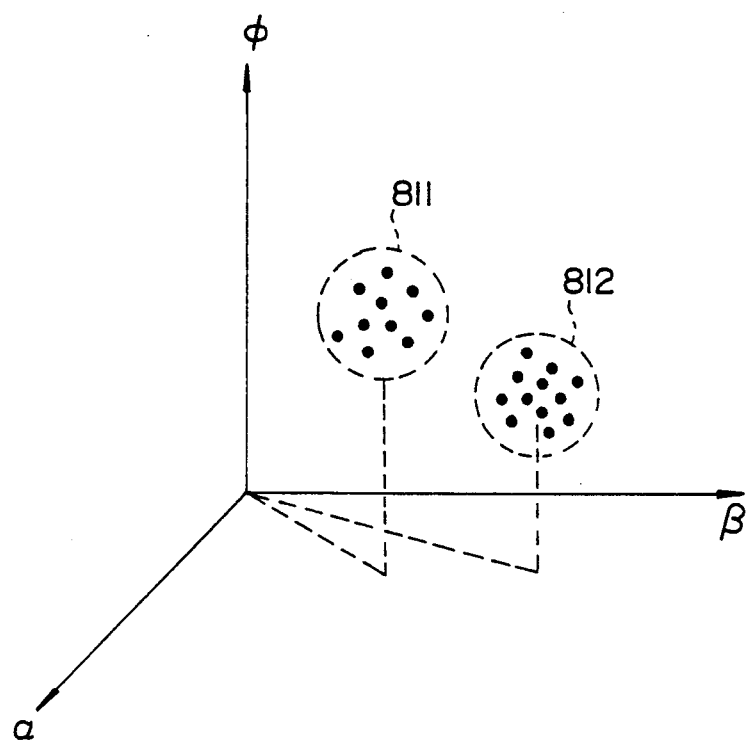
FIG. 12 is a diagram showing the relation of $\phi$ with respect to $\alpha$ and $\beta$ in the FIG. 4 apparatus.

FIG. 12 shows the relation of work function $\phi$ in the specimen 401 with respect to the parameters $\alpha$ and $\beta$ in equation (3) indicating the relation between the distance Z of AFM tip 631 from specimen 401 and the interatomic force f in the analysis apparatus 600 of FIG. 4. By plotting three-dimensionally as shown in FIG. 12 the values of $\alpha$ and $\beta$ calculated from measured values of f at two Z positions pursuant to equation (3) and the value of work function $\phi$ calculated from a measured value of $i_T$ pursuant to equation (2), a three-dimensional plot position 811 or 812 can be determined in compliance with the material of the specimen 401 and the kind of foreign matter. Thus, by measuring data of $\alpha$, $\beta$ and $\phi$ in advance in connection with known foreign matters, the kind of a foreign matter can be identified from a three-dimensional plot position of $\alpha$, $\beta$ and $\phi$ for an object being measured.

Figure 13:
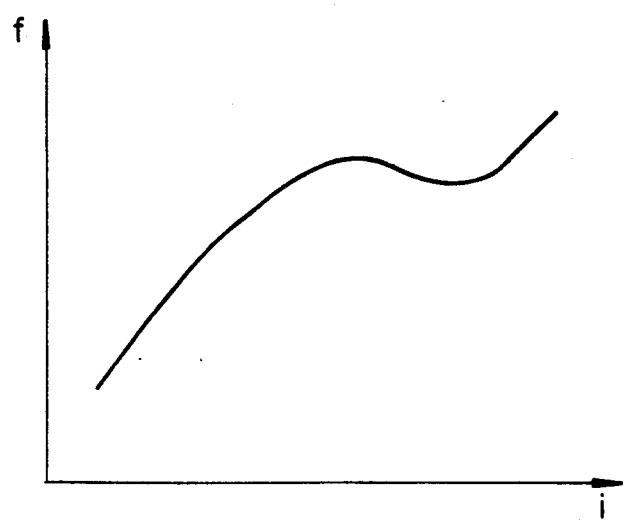
FIG. 13 is a graph showing the relation between tunnel current and interatomic force.

FIG. 13 graphically shows the relation between tunnel current i in the specimen 401 and interatomic force f in the FIG. 4 analysis apparatus 600, which relation is obtained through measurements of the tunnel current $i_T$ and interatomic force f of equation (3) carried out by changing the change $\Delta Z$ of distance Z while keeping the bias voltage V of FIG. 4 constant and may be used as a data base. The present-day level of study on techniques relevant to STM is not enough to clarify the correct corelation between tunnel current $i_T$ and interatomic force f as well as the relation between the kind of element and the tunnel current and interatomic force. But tunnel current $i_T$—interatomic force f spectra measured in advance for many substances related to materials of the specimen 401 and foreign matters can be used for identification of an object being measured. The spatial distribution of work function $\phi$ can also serve as a powerful means for element identification.

As described above, in the analysis apparatus 600, detected net signals are $i_A$, $i_T$, $V_A$ and $V_T$ alone and on the basis of data represented by these signals, the analysis data preparing unit 674 prepares analysis data as explained in connection with FIGS. 9, 11, 12 and 13. The analysis data is stored in the data storing unit 675 and then compared with analysis data of a newly detected and analyzed foreign matter at the data judging unit 676.

The information managing unit 673 is adapted to manage the STM XYZ fine movement controller 671 and STM rough drive controller 672 and it operates to control the STM such that information which the analysis data preparing unit 674 desires to acquire can be obtained.

Thus, as described above, the analysis data judging unit 676 does not always make a definite decision but it sometimes merely determines data close to any analysis data obtained precedently. Accordingly, it is effective that the data storing unit 675 stores in advance analysis data (FIGS. 9 to 13) for known substances.

Figure 16:
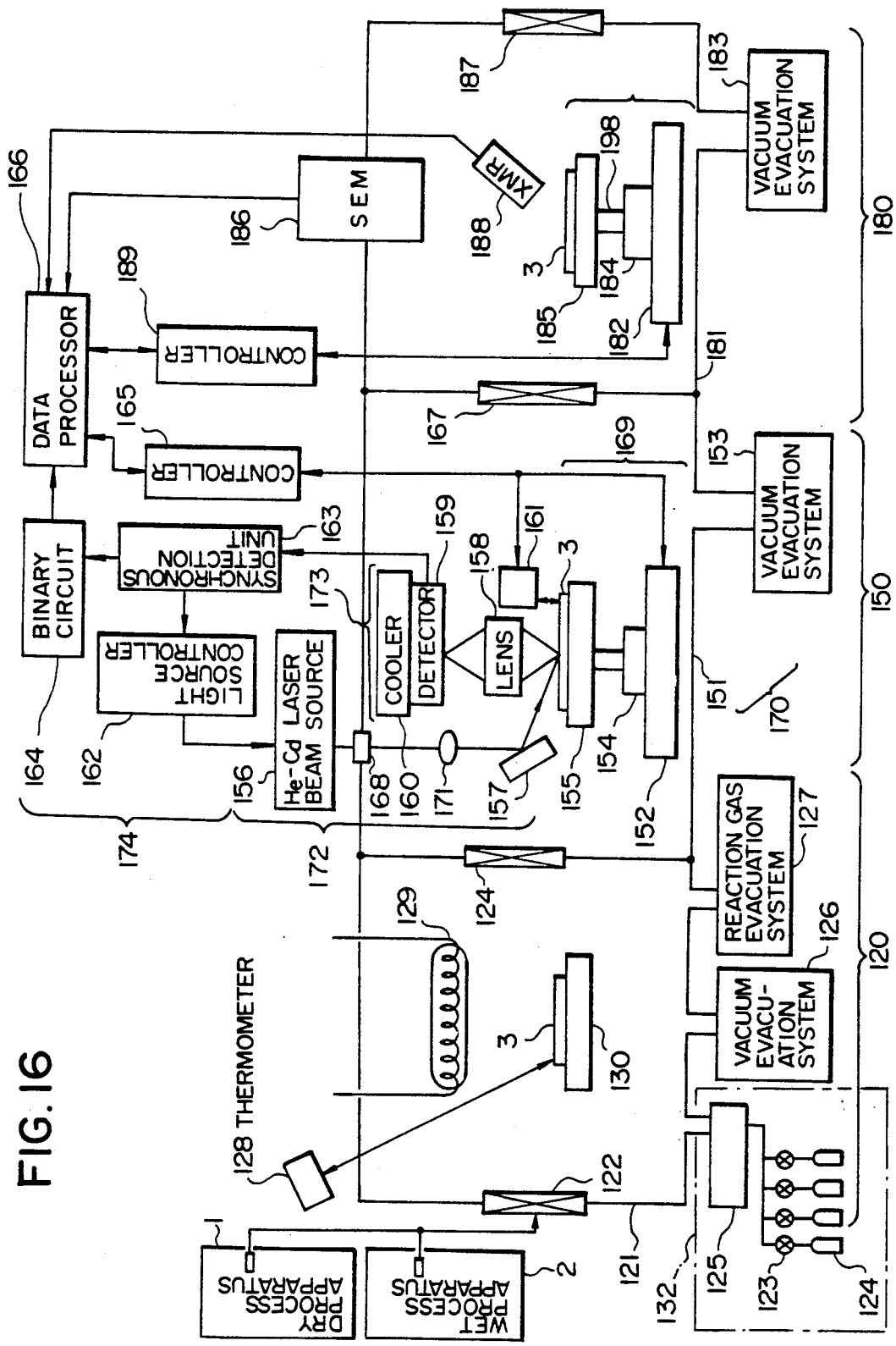
FIG. 16 is a schematic block diagram showing an embodiment of a contamination detecting apparatus according to the invention.

Further, a data processing unit 166 as shown in FIG. 16 has the data storing unit 675 and analysis data judging unit 676 shown in FIG. 4 and performs comparative analysis of foreign matters on the basis of data from the SEM 186 and XMR 188.

Namely, the data processing unit 166 is also grounded on the idea that although definite analysis cannot be accomplished, any one of foreign matters taking place in the semiconductor production line can be deduced based upon the comparative analysis.

The sampling apparatus 400, detecting apparatus 500 and analysis apparatus 600 of the off-line inspecting system 1002 corresponding to the mass production start-up in semiconductor production process, shown in FIG. 1, are used to obtain in advance measurements of elements of foreign matters having a possibility of mixing and to store the measurements as a data base so that the stored data may be compared with the results of measurement of an object being measured to permit classification of the kinds of elements of foreign matters. The concept of the above method neglects the correct, meaningful significance of the work function and the reasons of occurrence of other phenomena, thus lacking accuracies but is satisfactorily useful to meet the purpose of identifying elements of foreign matters and "deducing" generation sources.

Since individual units of the sampling apparatus 400, detecting apparatus 500 and analysis apparatus 600 of the inspecting system can be combined together through coordinate management so as to be always operated, the operation efficiency of each unit can be increased as compared to the conventional technique as disclosed in JP-A-60-218845 wherein individual units are coupled together as mechanisms and used. The coordinate management referred to herein signify a technique by which data indicative of coordinates of a position, within a wafer, of a foreign matter detected by the detecting apparatus 500 is transferred to the analysis apparatus to allow the same to instantaneously find a location where the foreign matter is present and analyze the foreign matter. In addition, the performance of each unitary unit can be improved easily because disadvantages resulting from the prior art having the individual units coupled as mechanisms, such as an increase in vibration of the whole system due to disturbance of balance of vibrations and an increase in electrical noise due to disturbances of balance of electromagnetic fields of the whole system, can be eliminated.

In the dealing system 700 of the off-line inspecting system 1002 corresponding to the mass production start-up in semiconductor production process, a generation source of foreign matter is deduced on the basis of information concerning a foreign matter on the specimen detected and analyzed by means of the sampling apparatus 400, detecting apparatus 500 and analysis apparatus 600, and a countermeasure for preventing an object in a mass production line considered as the generation source from generating dusts is undertaken, the countermeasure being evaluated by comparing the number of foreign matters generated before execution of the countermeasure with that after execution of the countermeasure.

The deduction of the foreign-matter generation source will be described with reference to FIG. 23. Information concerning a foreign matter obtained from the analysis apparatus 600 contains the size of the foreign matter, constituting elements, binding condition of elements and the like. A unit, use material or unit material which meets most the conditions of the foreign matter is selected from Table of FIG. 23 in order to deduce a unit or material which behaves as a cause of foreign-matter generation.

Alternatively, the deduction, countermeasure and evaluation can be carried out during start-up of mass production of LSI's by providing a monitor for sensing apparatus 200 which can manage easily on real time the process, unit, material or atmosphere of the on-line foreign matter inspecting system 1001 corresponding to a mass production line which is found to be a dust generation source for foreign matter generation. This sensing apparatus 200 may also handle a sampling wafer but typically it monitors a product wafer 406. Also, during mass production, the unit, process and other factors are normally supervised by means of the monitors of the sensing apparatus 200 disposed in the on-line foreign matter inspecting system 1001 and in the event of occurrence of abnormality, cause hunting is effected by the off-line inspecting system 1002.

The sensor of the sensing apparatus 200 of the on-line inspecting system 1001 corresponding to the mass production start-up in semiconductor production process will now be described by way of in-vacuum dust occurrence monitor 204. In vacuum, there is no medium for transporting dusts and the air dust monitor cannot be used. But the present embodiment of the invention positively takes advantage of this counter fact that no medium for transporting dusts exists in vacuum. More specifically, in the absence of medium for transporting dusts in vacuum, the dusts will drop by gravity, will be attracted mutually by electrostatic force or will be moved randomly under the influence of Brownian motion but especially, exertion of the former two types of force is predominant in vacuum. Accordingly, a technique is contrived which utilizes the two types of force to count the number of dusts in vacuum.

Figure 14:
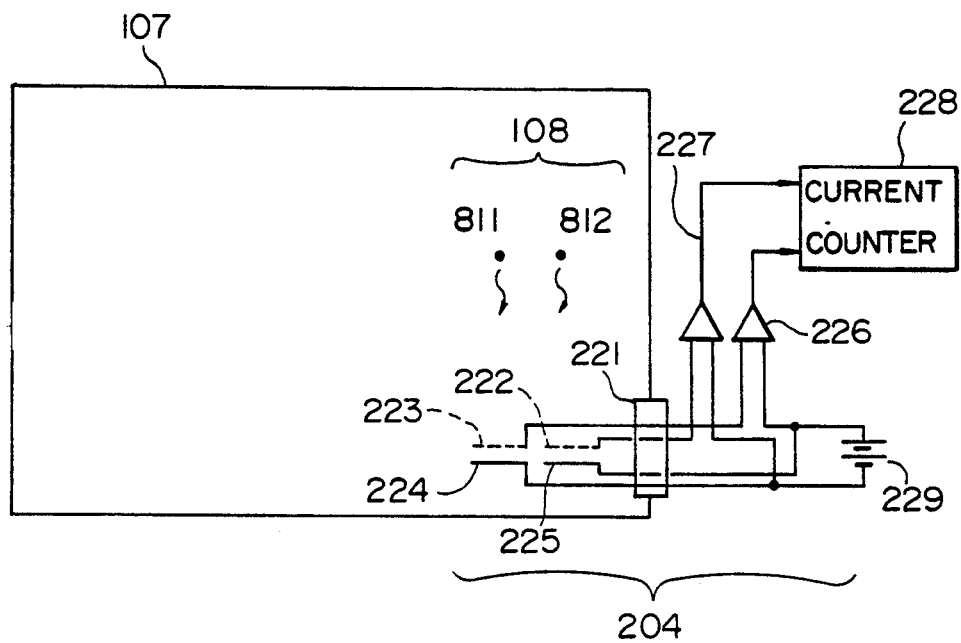
FIG. 14 is a schematic block diagram showing an embodiment of an in-vacuum dust occurrence monitor of a sensing apparatus in FIG. 1.

FIG. 14 is a schematic block diagram showing an embodiment of the in-vacuum dust occurrence monitor 204 of the sensing apparatus in FIG. 1. Referring to FIG. 14, the in-vacuum dust occurrence monitor 204 is placed at a location 108 in vacuum processing unit 107 which may behave as a foreign matter generation source and it comprises a port 221, a cathode grid electrode 222, an anode grid electrode 223, an anode plate 225, a cathode plate 224, an electric power supply 229, ammeters 226 and 227 and a current counter 228. The electric power supply 229 applies DC voltage between the cathode grid electrode 222 and anode plate electrode 225 and between the anode grid electrode 223 and cathode plate electorde 224, and the ammeters 226 and 227 are of high sensitivity with can measure even one electric charge.

The operation of the monitor constructed as above will now be described by referring to an instance where a foreign matter 811 or 812 takes place and travels toward the anode grid electrode 223 or cathode grid electrode 222. If an excited electron is present on the foreign matter 811, the anode grid electrode 223 captures the electron when the foreign matter 811 passes by the anode grid electrode 223 and concurrently therewith the foreign matter 811 is positively charged and attracted to the cathode plate electrode 224. As a result, current from the application power supply 229 flows between the cathode plate electrode 224 and anode grid electrode 223 and can be detected by the ammeter 226.

The number of frequencies of current conduction can be counted by the current counter 228 in order to count the number of reaching foreign matters 811. On the other hand, fi the foreign mater 812 is conditioned to be difficult to discharge an electron when passing by the cathode grid electrode 222, the foreign matter 812 accepts an electron from the cathode grid electrode 222 and the negatively charged foreign matter reaches the anode plate electrode 225. At the time, current flows and detected by the ammeter 227. The number of frequencies of current conduction can be counted by the current counter 228 in order to count the number of reaching foreign matters 812.

The in-vacuum dust occurrence monitor 204 shown in FIG. 14 has been described as having both the cathode grid electrode type and anode grid electrode type but in some applications, even a monitor having either one of the two types does well. For convenience of explanation, the foreign matter 811 or 812 has been exemplified as being easy to accept an electron or to release an electron, bu this is not limitative and thanks to the forcible application of voltage, any kinds of particles can be counted. Presumbly, however, the foreign matter of the type as described previously which is not disturbed by the positive and negative voltages during traveling can be counted more accurately.

Figure 15:
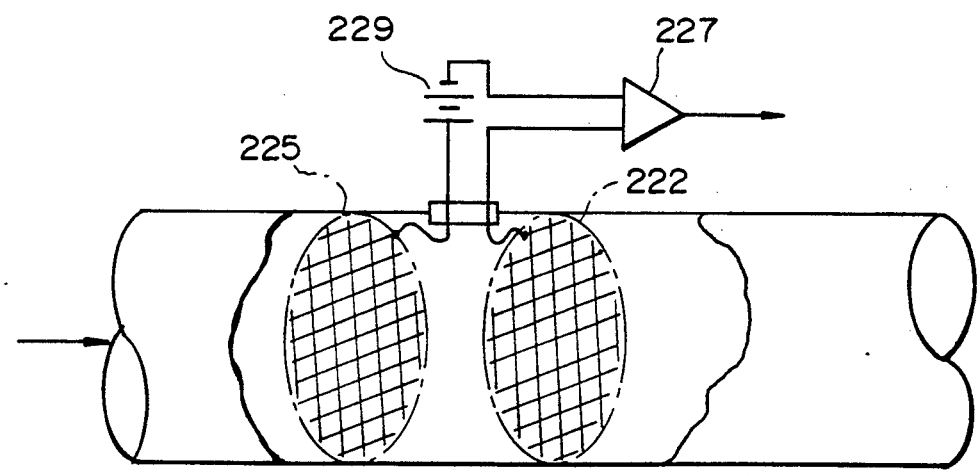
FIG. 15 is a schematic perspective view showing another embodiment of the in-vacuum dust occurrence monitor of the sensing apparatus in FIG. 1.

FIG. 15 is a schematic perspective view showing another embodiment of the in-vacuum dust occurrence monitor 204 of the sensing apparatus 200 in FIG. 1. In the FIG. 15 embodiment, the in-vacuum dust occurrence monitor 204 is disposed in a piping system of vacuum processing unit in place of the vacuum processing unit 107 of FIG. 14. In this in-vacuum dust occurrence monitor 204, current flowing between a cathode grid electrode 222 and an anode grid electrode 225, which are disposed in a piping 107, is detected by an ammeter 227 in order that the number of traveling foreign matters carried on gases flowing through the piping 109 can be counted by the current counter.

According to the foregoing embodiment, the whole system is divided into the foreign matter inspecting system for the mass production start-up in semiconductor production process and the foreign matter inspecting systm for the mass production line in semiconductor production process, so that the function of detecting, analyzing and evaluating foreign matters which is required during the mass production start-up can be maximized to promote smooth feedback to the mass production line and reduce the mass production start-up period.

Figure 22:
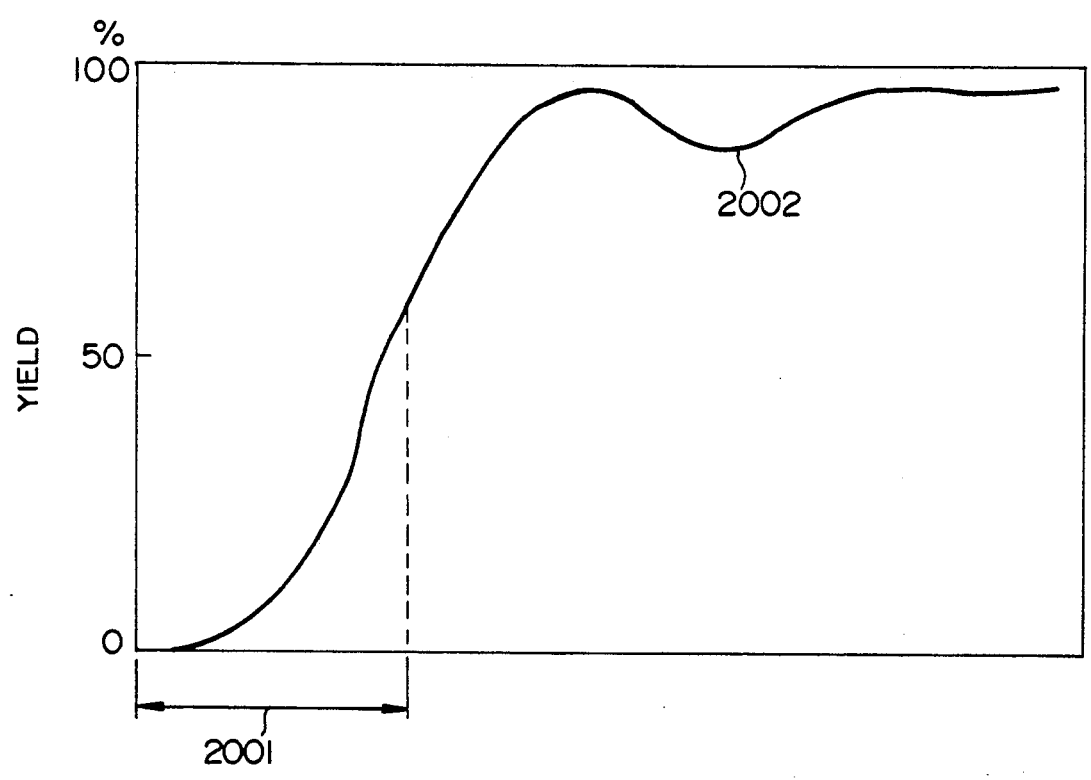
FIG. 22 is a graph showing the change of yield to explain "mass production start-up period"

The term "mass production start-up period" will be described. FIG. 22 shows the change of yield of mass production line. As will be seen from FIG. 22, the yield rises gradually near 0%, ultimately reaching a high yield of 90% or more. The mass production start-up in semiconductor production line is reserved for the yield to rise up to a high level and a period of time 2001 within which the yield rises to reach approximately several of tens of percent is called the mass production start-up period.

At a depression 2002 in FIG. 22, the yield goes down temporarily and one object of the on-line foreign matter inspecting system 1001 according to the present invention is to predict the depression 2002 and undertake the previously-described foreign-matter countermeasure for preventing the occurrence of the depression 2002.

Referring now to FIGS. 16 to 21, another embodiment of the invention directed to contamination detecting method and apparatus usable in the semiconductor prodction process shown in FIG. 1 will be described.

FIG. 16 shows an example of construction of a contamination detecting apparatus. As shown, in this example, the apparatus generally comprises a contamination detection auxiliary unit 120, a contamination detection unit 150 and a contamination analysis unit 180. The contamination detection auxiliary unit (heating unit for a substrate acting as a specimen) 120 has a vacuum chamber 121 as a main component. A specimen (a substrate: specifically, a wafer, a substrate for liquid crystal television formed with TFT) 3 is introduced into the vacuum chamber 121 externally through a specimen inlet port 122, heated by an infrared ray heater 129 while being carried on a carriage 130 and after heating, sent to the contamination detection unit 150 through a specimen outlet/inlet port 124. During heating, the heating temperature is measured by means of a thermometer 128 and atmosphere inside the vacuum chamber 121 is set and controlled by means of a gas-reaction gas supply system 132, a reaction gas evacuation system 127 and a vacuum evacuation system 126. For example, the infrared ray heater 129 serving as a heating source, the thermometer 128 serving as a temperature measuring means and the atmosphere setting and control will now be described briefly.

Firstly, in place of the infrared ray heater 129, a filament type heater (such as halogen lamp or tungsten lamp) and a laser beam source (such as Ar laser, excimer, YAG laser or $CO_2$ laser) may be used as the heating source. By focusing a laser beam from a laser beam source onto the specimen 3 and scanning the focused beam thereon, the specimen 3 can be heated with ease. With this method, only a limited region on a wafer can be treated to ensure that when regions for contamination evaluation are formed on a TEG (Test Element Group) on a wafer in the course of production of devices, contaminants generated in individual processes can be evaluated.

As the temperature measuring means, an infrared radiation type and a diffracted beam detection type (such as described in JP-A-62-88929) may be used which measure directly the temperature of the specimen 3; alternatively, the temperature of the carriage 130 carrying the specimen 3 may be measured. For measurement, a contact type thermometer such as a thermocouple may also be used.

Then, to explain the atmosphere setting and control, as the vacuum evacuation system 126 for vacuumevacuating the interior of the vacuum chamber 121, any of rotary pump, oil diffusion pump and turbo molecular pump may be used, provided that the employed pump has the performance enough to maintain a sufficient degree of vacuum to prevent an unexpected reaction of the specimen 3 with gas molecules in the atmosphere during the heat treatment. Specifically, a degree of vacuum of about $10^{-8}$ Torr is desirable and to this end, preferably, rough evacuation is first effected with a rotary pump, followed by further evacuation with, for example, a turbo molecular pump. The reaction gas evacuation system 127 is constructed as a vacuum evacuation system but for vacuum evacuation, only the vacuum evacuation system 126 may normally be used. Especially, the reaction gas evacuation system 127 is used when the reaction gas is a poisonous gas or a reactive gas; and it may otherwise be used in combination with the vacuum evacuation system 126 in the event that the evacuation performance of the vacuum evacuation system 126 is insufficient. One or more kinds of gases such as $O_2$, $N_2$ and $CF_2$ are stored in gas cylinders 124 inside the reaction gas supply system 132 and one or more kinds of these gases are selectively mixed by means of mixers 123 and supplied to the vacuum chamber 121 through a flow rate controller 125.

Following the description of the contamination detection auxiliary unit 120 given above, the contamination detection unit 150 will now be described. This unit 150 includes a stage system 169, a vacuum chamber system 170, a light source system 172, a scattered beam detection system 173 and a signal processing system 174. As shown, in the stage system 169, a specimen 3 is carried on a Z stage 168, a $\theta$ stage 154 and an X stage 152 through the medium of a pedestal 155 so as to be rotatable and movable in X and Z directions. The vacuum chamber system 170 includes a vacuum chamber 151 provided with specimen outlet/inlet ports 124 and 167 and a vacuum evacuation system 153 for vacuum evacuating the vacuum chamber 151, and the light source system 172 includes a He-Cd laser beam source (having a wavelength of 325 nm) 156, an optical window (forming a part of partition wall of the vacuum chamber 151) 168, a focusing optics 171 and a mirror (for scanning) 157. Further, the scattered beam detection system 173 includes an objective lens 158, a detector 159 and a cooler (for cooling the detector 159) 160, and the signal processing system 224 includes a light source turn on/off controller 162, a synchronous detection circuit 163, a binary circuit 164 and a data processor 166. In this example, only the detector 159 is cooled to about $-180°$ C. with liquid nitrogen but an analog section comprised of the synchronous detection circuit 163 and binary circuit 164 may also be cooled, with the aim of reducing noise in the analog section by cooling.

After a specimen 3 is placed on the pedestal 155, the stage system 169 is fine adjusted such that the specimen is positioned on the focal plane of the scattered beam detection system 173 by means of an autofocus system 161 under the control of a controller 165. After completion of the fine adjustment, the X stage 152 is moved while the $\theta$ stage 154 being rotated in order that the entire surface of the specimen 3 is scanned with a laser beam spot from the mirror 157. For example, as the autofocus system 161, any suitable type such as a stripe pattern projecting type or laser oblique irradiation type may be employed.

Figure 17:
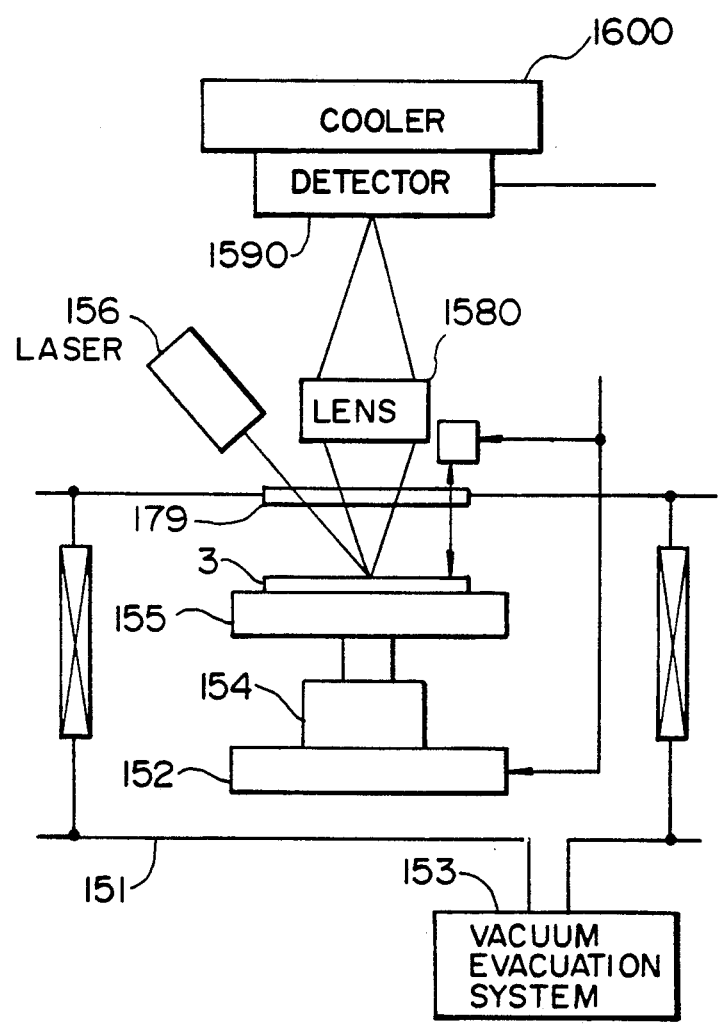
FIG. 17 is a schematic block diagram showing another embodiment of a scattered beam detection system shown in FIG. 16.

FIG. 17 illustrates another example of construction of the scattered beam detection system 173. As shown, it will do that an objective lens 1580 and a detector 1590 may be disposed externally of the vacuum chamber 151, provided that an optical window (forming a part of partition wall of the vacuum chamber 151) 179 is necessarily mounted. Further, the objective lens 1580 must have undergone aberration correction in which the thickness and position of the optical window are involved. In some cases, the optical window 179 may be constructed as a part of the objective lens 1580.

Figure 18:
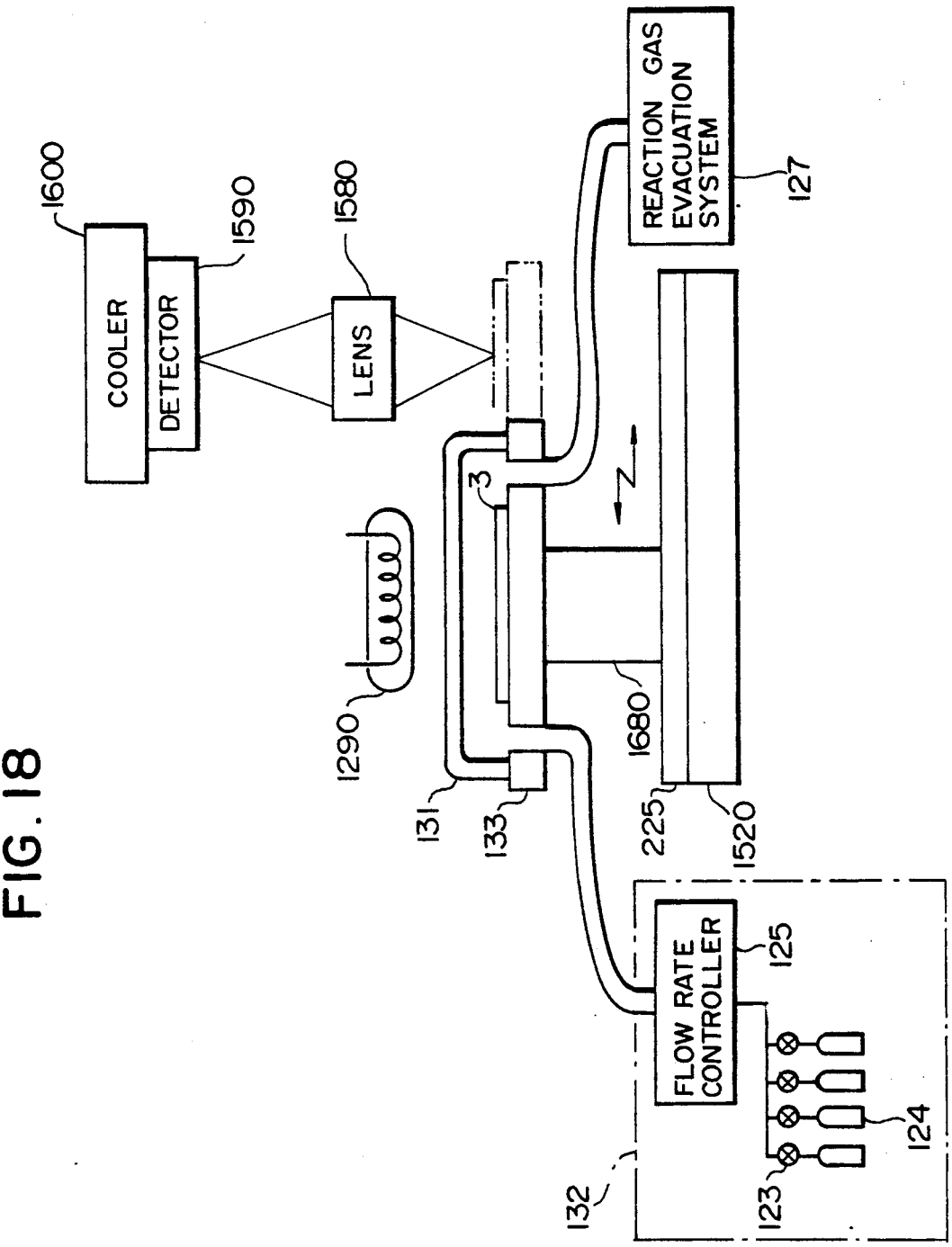
FIG. 18 is a schematic block diagram showing another embodiment of a contamination detection auxiliary unit shown in FIG. 16.
Figure 19:
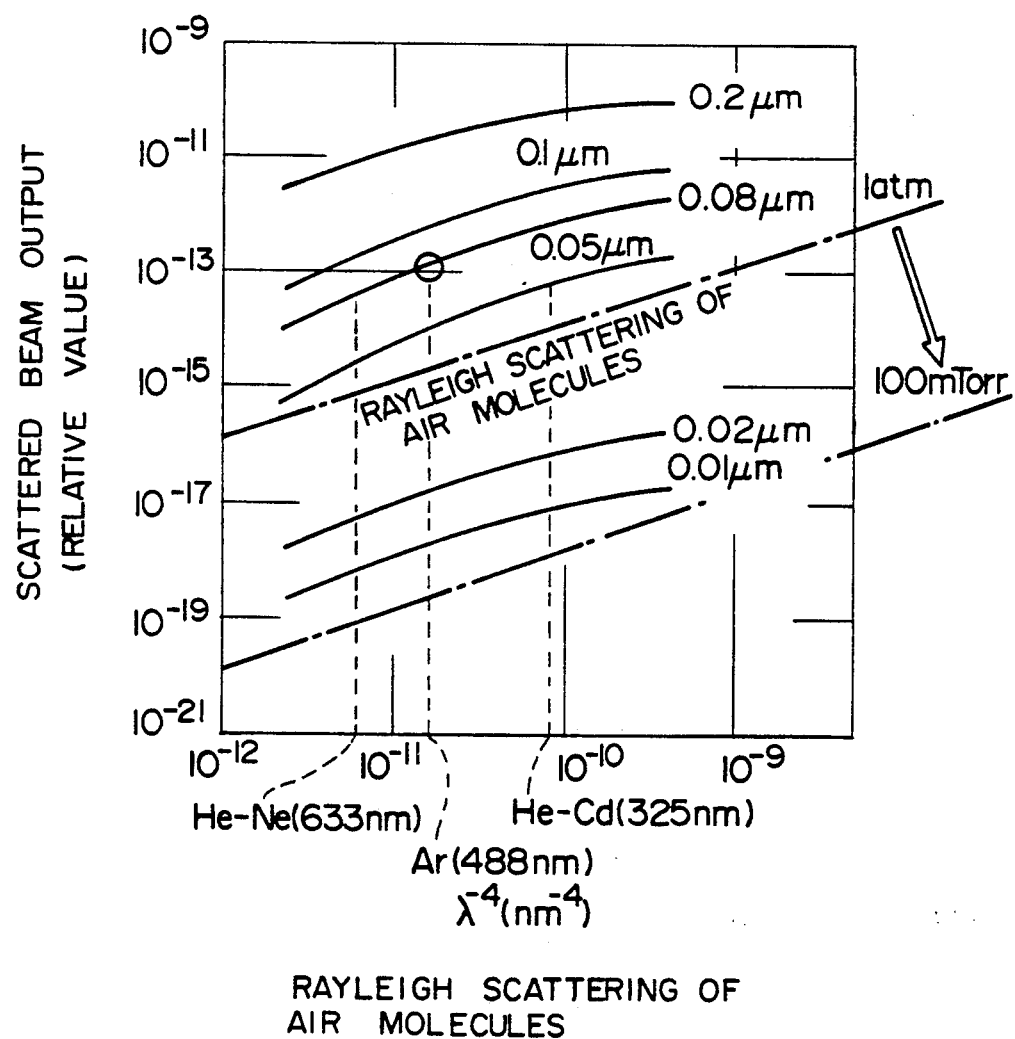
FIG. 19 is a graph useful to explain how Rayleigh scattering due to air molecules changes with the condition of barometric pressure.

FIG. 18 shows an example where an infrared ray heater 1290 forming a part of the contamination detection auxiliary unit 120 is disposed externally of the vacuum chamber 121. In this case, the whole of the vacuum chamber 121 is constructed as a specimen chamber 133. The specimen chamber 133 per se is movable toward the contamination detection unit 150 so as to be positioned directly beneath the objective lens 1580, and a part of partition wall of the vacuum chamber 121 is constructed as an optical window 131. When the vacuum chamber 121 is moved toward the contamination detection unit 150 (part of specimen 3 and the like are indicated at dotted line), a scattered beam generated inside the specimen chamber 133 transmits through the optical window 131 of the specimen chamber 133 and is detected externally of the vacuum chamber 121. Excepting the above, the construction is identical to that shown in FIG. 16. In the stage system 169 of this example, a Y stage 225 substituting for the $\theta$ stage 154 overlies an X stage 1520 to meet the requirement that the vacuum chamber 121 be moved toward the contamination detection unit 150. Of course, the $\theta$ stage 154 and Y stage 225 may be used in combination. In FIG. 18, illustration of the autofocus system is omitted.

Returning to FIG. 16, the contamination analysis unit 180 will now be described. Contamination analysis at the contamination analysis unit 180 is carried out in a vacuum chamber 181 under the control of a controller 189. Inside the vacuum chamber 181 having the specimen outlet/inlet port 167, a specimen outlet port 187 and a vacuum evacuation system 183, there are provided a pedestal 185, a Z stage 198, a $\theta$ stage 184 and an X stage as well as a scanning electron microscope 186 adapted to analyze contaminants. Preferably, the scanning electron microscope 186 is attached with a secondary X-ray spectroscopic (XMR) means 188. The scanning electron microscope 186 may be replaced with a scanning tunneling microscope or a secondary ion mass spectroscopic means.

To describe the overall operation, the contamination detecting apparatus of FIG. 16 according to the invention evaluates foreign matters and contaminants present on the specimen 3 to ultimately evaluate the degree of cleanness of various LSI production apparatus (for example, a dry process apparatus 1 such as etching apparatus, CVD apparatus, sputtering apparatus and exposure apparatus or a wet process apparatus 2 such as washing apparatus and wet etching apparatus). Upon evaluation, a dummy specimen for contamination is passed through an LSI production apparatus and subsequently it behaves as a specimen 3 which is first placed in the contamination detection auxiliary unit 120. When TEG (test element group) regions on a wafer, as described previously, are used, a specimen in the course of production of devices may be used in place of the dummy specimen. In the contamination detection auxiliary unit 120, the specimen 3 is heated prior to contamination detection. The reason for the necessity of heating in this phase is clear from the literature mentioned previously, i.e., the Japanese Journal of Applied Physics, Vol. 27, No. 10, October 1988, pp. L1819 to L1821. The literature reports that through heat treatment conducted at 1150° C. for one hour in $N_2$ atmosphere, $Cu_6Si$ of $0.2 \times 0.2$ $\mu$m and about 0.5 $\mu$m depth is precipitated and formed at a defect in the surface of a Si substrate. The literature does not detail the reason for occurrence of this phenomenon but simply explains that this phenomenon is due to the fact that Cu atoms contained in the Si substrate are diffused by heat treatment and adsorbed on the defect under the influence of gettering. Analogically, it is expected that a similar phenomenon takes place in other metal than Si having a small solid solubility in Si, for example, Fe, Cr and W.

To take advantage of the above phenomenon, in the contamination detection auxiliary unit 120, the specimen 3 is subjected to heat treatment at about 1000° C. for about one hour. Values of treatment temperature and treatment time referred to herein are mere reference values which are not limitative and can be set suitably. In order to stablize the aforementioned phenomenon due to heating, there is formed in the surface of the specimen 3 a crystalline defect (flaw) which forms a low potential portion. This flaw acts as a nucleus for contaminant precipitation. The flaw must however be small enough not to cause noise when detecting whether any contaminant is precipitated or not. Specifically, the size of the flaw is preferably 0.01 μm or less. For formation of this flaw, the scanning tunneling microscope can be used effectively as described in a literature (Nanometer Scale Structuring of Silicon by Direct Indentation). Further when a specified kind of gas is selected to establish atmosphere inside the vacuum chamber 121, only a specified element can be grown selectively. The usable gas is an oxidizing gas such as $O_2$, $N_2$, $Cl_2$ of $F_2$.

To describe the operation of the contamination detection unit 150, the heat treated specimen 3 is then placed on the pedestal 155 and the surface height of the specimen 3 is so adjusted as to be flush with the focal plane of the scattered beam detection system 173. Thereafter, the whole surface of the specimen 3 is scanned with a laser beam spot while the specimen 3 being rotated by means of the 8 stage 154 and moved in the X direction by means of the X stage 152. When a foreign matter or a contaminant exists at a scanning position, the laser beam is scattered by the foreign matter or contaminant and a scattered beam passing through the objective lens 158 is detected by the detector 159. Thus, the detection of the scattered beam can determine the presence of the foreign matter or contaminant. Since in this example the vacuum chamber 151 is evacuated to vacuum prior to detection of contaminants, generation of unwanted Rayleigh scattering can be minimized and consequently the scattered beam can be detected at a high S/N ratio by means of the detector 159. In place of being evacuated to vacuum, the interior of the vacuum chamber 151 may be filed with atmosphere of a specified gas (which is less prone to Rayleigh scattering than air) or brought into low temperature condition, thus attaining similar effects. By bringing the interior of the vacuum chamber 151 into low pressure condition, the generation of scattered beam can also be suppressed as evidence by curves in FIG. 19. Curves in this figure are representative of values calculated by consulting "Principle III of Optics" by Macks Bolln and Emil Wolf (both of phonetic spelling), translated by Tohru Kusakawa and Hidetsugu Yokota (Tokai University Publisher, pp. 950–962). Data in FIG. 19 demonstrates that the scattered beam output due to Rayleigh scattering by air molecules at 1 atm or less has the same level as the scattered beam output due to a foreign matter of a size of about 0.05 μm. Accordingly, under the normal existence of air, the foreign matter size as such defines a detection limit. However, vacuum evacuation of the interior of the vacuum chamber 151 to, for example, a reduced pressure of 100 mTorr makes it possible to detect a foreign matter having a size of about 0.01 μm. The operation of the contamination analysis unit 180 is not directly related to the present invention and will not be described herein.

The contamination detecting apparatus according to the embodiment of the invention has been described and this apparatus can be incorporated in the semiconductor production line. When the contamination detecting apparatus are provided at the substrate outlet and inlet ports of individual vacuum processing units constituting the semicondcutor production line, the contamination condition can be managed easily before and after processing by each vacuum processing unit.

Figure 24:
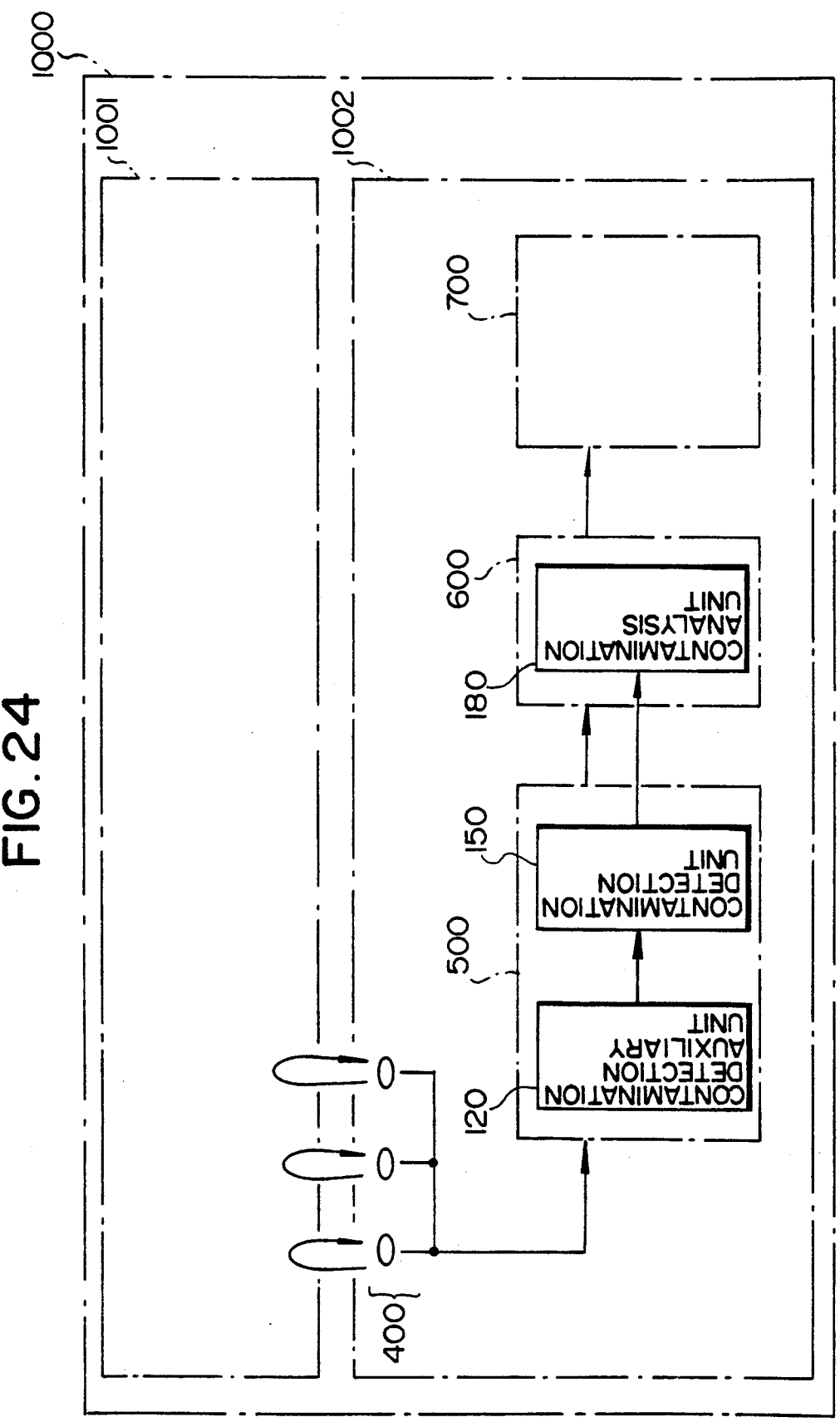
FIG. 24 is a block diagram showing an example of application of the FIG. 16 contamination detecting apparatus to the FIG. 1 embodiment.

As an example, FIG. 24 shows a layout of the previously-described contamination detecting apparatus in the foreign matter detecting system 1000 for the mass production start-up and mass production line in semiconductor production process. A wafer 3 is sampled by the sampling apparatus 400, heat-treated at the contamination detection auxiliary unit 120 of the detecting apparatus 500 and sent to the contamination detecting unit 150 where a contaminant is detected. The wafer 3 is then sent, along with coordinates of a position where the contaminant is detected, to the contamination analysis unit 180 in which the contaminant is analyzed. Results of analysis are sent to the dealing system 700.

With the only exception of the above, the construction and operation of each block resembles that of each block in the embodiment of FIG. 1.

Obviously, the application of the previouslydescribed contamination detecting method and apparatus according to the invention is not limited to the semiconductor production line but may also be directed to various fields including a single independent inspection process.

A method of preparing a specimen used for evaluation of the performance of the contamination detecting apparatus according to the present embodiment will now be described. For evaluation of the contamiantion detecting apparatus, it is necessary to deposit fine particles each having a size of about 0.01 μm to 0.03 μm on a specimen but practically, in the past, much difficulties have been encountered in obtaining a specimen deposited with such fine particles. Namely, when standard fine particles of, for example, polystyrene are used, the position on the specimen at which fine particles are deposited becomes unlocated and a mixture in ultrapurity is condensed, thus making it difficult to obtain a proper specimen for performance evaluation.

Figure 20:
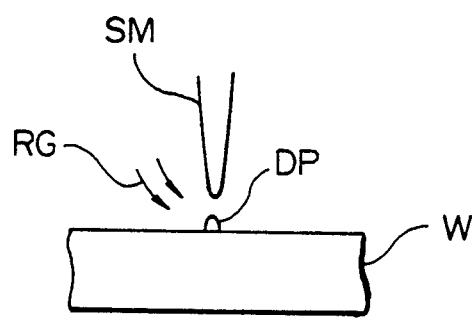
FIG. 20 is a diagram for explaining a deposition particle preparation method according to an article.
Figure 21:
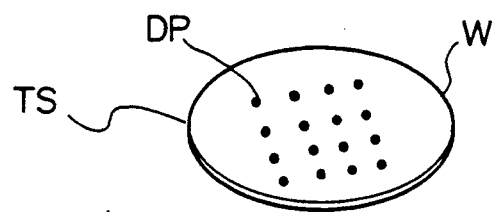
FIG. 21 is a perspective view of a specimen according to the invention used for evaluating the performance of the contamination detecting apparatus.

Incidentally, an article in pages 1877 to 1880 of "Journal of Science and Technology B6, Nov/Dec. 1988" reports that a deposition particle having a size of 0.02 to 0.03 μm is prepared. As shown in FIG. 20, a scanning tunneling microscope SM and tungsten carbonyl (W(CO)6) serving as a reaction gas RG are used to prepare a deposition particle DP of the above size on the surface of a wafer W, and by using such a technique, a specimen for performance evaluation can be obtained. As shown in FIG. 21, deposition particles DP are deposited substantially regularly on the surface of a performance evaluation specimen DP and accordingly, the positions of deposition particles can be located more clearly than those of standard particles to ensure that the evaluation can be effected quantitatively and rapidly.

According to the above embodiment, the contamination detecting apparatus can be obtained which can detect with high accuracies foreign matters or contaminants present on a substrate or contaminative elements present in a substrate. Further, in individual vacuum processing units constituting a semiconductor line, the degree of contamination of a substrate standing for an object to be processed and the presence or absence of foreign matters can be evaluated and detected with ease.

We claim:

1. In a method of manufacturing semiconductors by processing semiconductor wafers through a semiconductor production apparatus group or line having a utility group including a gas supplier means and a water supplier means and a plurality of production apparatus located in a predetermined processing atmosphere, the method comprising a foreign substance inspection method for mass production start-up and mass-production line for manufacture of semiconductors, the inspection method including the steps of:

for mass production start-up, supplying at least one sampling wafer to at least one of the gas supplier means, the water supplier means and the plurality of production apparatus so as to process the supplied at least one sampling wafer in accordance therewith and to determine generation of a foreign substance and a contaminant;

collecting the at least one processed sampling wafer and utilizing an off-line inspecting system having a detecting apparatus for detecting the collected sampling wafer to determine whether the collected sampling wafer contains a foreign substance inclusive of a contaminant and for detecting a foreign substance existing position, an analysis apparatus for identifying at least a kind of the detected foreign substance on the basis of the detected foreign substance existing position, and a system for investigating at least causes of generation of the detected foreign substance on the basis of the identified kind of the foreign substance so as to enable mass production of semiconductors by enabling control of the plurality of production apparatus and the utility group in dependence upon the identified generation causes so as to enable removal thereof; and for mass production of semiconductors, utilizing an on-line foreign substance control and inspecting system including sensing apparatus with monitors located selectively along the production apparatus line and a control system for controlling the sensing apparatus wherein the monitors enable monitoring of data of parameters including temperature, dust generated within and between the production apparatus, water, gas and pressure, which parameters effect abnormal generation of foreign substances inclusive of contaminants and thereby enable detection of changes in monitor data of the parameters.

2. A method according to claim 1, wherein the analysis apparatus for mass production start-up utilizes a scanning tunnelling microscope/spectrometer (STM/STS) to identify the kind of the detected foreign substance.

3. A method according to claim 2, further comprising the step of storing previously obtained data of relationship of kinds of foreign substances and analysis data thereof identified by the STM/STS as a data base, and identifying the kind of the detected foreign substance presently being analyzed by comparing the data base and the presently obtained analysis data obtained by analyzing the detected foreign substance by the STM/STS.

4. A method according to claim 1, wherein the detecting apparatus of the off-line inspecting system optically detects the foreign substance and includes an atmosphere surrounding a table for supporting thereon the sampling wafer wherein the atmosphere is adjusted to suppress Rayleigh scattering of light, conveying means for conveying and setting the sampling wafer on the table, laser beam means for radiating and focusing a laser beam on a surface of the sampling wafer set on the table, and light condensing detection means including photo-electric conversion means for condensing a laser beam focused on the sampling wafer surface and scattered by the foreign substance thereon and for receiving the condensed and scattered beam by the photo-electric conversion means to produce a foreign substance indication signal and to enable detection of the foreign substance existing position on the basis of the produced foreign substance indication signal.

5. A method according to claim 4, further comprising the steps of heating the sampling wafer to expedite eduction of the foreign substance on the sampling wafer surface, and conveying and setting the heated sampling wafer on the table by the conveying means.

6. In a system for producing semiconductors by processing semiconductor wafers by a semiconductor production apparatus group or line having a utility group including gas supplier means and a water supplier means, a plurality of production apparatus, and a foreign substance inspection system for mass production start-up and mass production line for manufacture of semiconductors, comprising:

an off-line inspection system for mass production start-up for enabling semiconductor mass production by applying countermeasures with respect to causes of foreign substances generated in the apparatus group or line, the offline inspection system including sampling apparatus for supplying at least one sampling wafer to at least one of the gas supplier means, the water supplier means and the plurality of production apparatus so as to process the supplied at least one sampling wafer in accordance therewith and to determine generation of a foreign substance and a contaminant, a detecting apparatus for detecting whether a process sampling wafer contains a foreign substance inclusive of a contaminant and for detecting a foreign substance existing position from the process sampling wafer, an analysis apparatus for analyzing data of the foreign substance detected in the process sampling wafer for identifying at least a kind of the foreign substance on the basis of the foreign substance existing position detected by the detecting apparatus, and means for investigating causes of generation of the foreign substance on the basis of the detected kind of the foreign substance; and an on-line foreign substance inspection system for mass production of semiconductors including sensing apparatus with monitors located selectively along the production apparatus line and a control system for controlling the sensing apparatus when the monitors enable monitoring of data parameters including temperature, dust generated within and between the production apparatus, water, gas and pressure, which parameters effect abnormal generation of foreign substances inclusive of contaminants and thereby enable detection of changes in the monitor data of the parameters.

7. A system according to claim 6, wherein the analysis apparatus for mass production start-up includes a scanning tunnelling microscope/spectrometer (STM/STS) to identify the kind of the detected foreign substance.

8. A system according to claim 7, further comprising means for storing previously obtained data of relationship of kinds of foreign substances and analysis data thereof identified by the STM/STS as a data base, the analysis apparatus identifying the kind of the detected foreign substance presently being analyzed by comparing the data base and the presently obtained analysis data obtained by analyzing the detected foreign substance by the STM/STS.

9. A system according to claim 6, wherein the detecting apparatus of the off-line inspecting system includes means for optically detecting the foreign substance and includes an atmosphere surrounding a table for supporting thereon the sampling wafer wherein the atmosphere is adjusted to suppress Rayleigh scattering of light, conveying means for conveying and setting the sampling wafer on the table, laser beam means for radiating and focusing a laser beam on a surface of the sampling wafer set on the table, and light condensing detection means including photo-electric conversion means for condensing a laser beam focused on the sampling wafer surface and scattered by the foreign substance thereon and for receiving the condensed and scattered beam by the photo-electric conversion means to produce a foreign substance indication signal and to enable detection of the foreign substance existing position on the basis of the produced foreign substance indication signal.

10. A system according to claim 9, further comprising means for heating the sampling wafer to expedite eduction of the foreign substance on the sampling wafer surface, and the conveying means conveying and setting the heated sampling wafer on the table.

11. A system according to claim 9, wherein the detecting apparatus includes focusing adjusting control means for controlling the laser beam focused by the laser beam means to generate a focused beam point on the sampling wafer surface.

12. A system according to claim 6, wherein the foreign substance detecting apparatus of the off-line inspecting system is disposed at at least one of substrate outlet and inlet ports of individual vacuum processing units for production of the semiconductors.

13. A system according to claim 12, wherein the foreign substance detecting apparatus includes an atmosphere setting/maintaining system for providing a specified atmosphere in which Rayleigh scattering is suppressed and for enabling detection of only a scattered beam from a foreign substance in the specified atmosphere.

14. A system according to claim 6, wherein the foreign substance detecting apparatus comprises:
a stage system for carrying said sampling wafer movable in X, Y and Z directions and rotatably on an XY plane;
an illumination light source system for causing a light spot to scan the whole surface of said sampling wafer in accordance with movement of said stage;
a scattered beam detecting system for detecting a scattered beam from a light spot position on said sampling wafer through photoelectric conversion;
a focus system for focusing, on said scattered beam detecting system, the scattered beam from the light spot position on said sampling wafer;
a signal processing system for processing the scattered beam detected by said scattered beam detecting system, in synchronism with scanning of the light spot; and
an atmosphere setting/maintaining system for producing a specified atmosphere in which Rayleigh scattering is suppressed and for enabling detection of only the scattered beam from the foreign substance in the specified atmosphere.

* * * * *